(12) United States Patent
Medin et al.

(10) Patent No.: US 12,351,639 B2
(45) Date of Patent: *Jul. 8, 2025

(54) ANTI-CD30 ANTIBODIES

(71) Applicants: Medical College of Wisconsin, Inc., Milwaukee, WI (US); University of Virginia Patent Foundation, Charlottesville, VA (US)

(72) Inventors: Jeffrey A. Medin, Shorewood, WI (US); Mary L Faber, New Berlin, WI (US); Everett R. Tate, Greendale, WI (US); Robyn A. A. Oldham, Milwaukee, WI (US)

(73) Assignees: The Medical College of Wisconsin, Inc., Milwaukee, WI (US); University of Virginia Patent Foundation, Charlottesville, VA (US)

( * ) Notice: Subject to any disclaimer, the term of this patent is extended or adjusted under 35 U.S.C. 154(b) by 2 days.

This patent is subject to a terminal disclaimer.

(21) Appl. No.: 18/163,667

(22) Filed: Feb. 2, 2023

(65) Prior Publication Data

US 2023/0235071 A1    Jul. 27, 2023

Related U.S. Application Data

(63) Continuation of application No. 16/580,483, filed on Sep. 24, 2019, now Pat. No. 11,584,799.

(60) Provisional application No. 62/735,508, filed on Sep. 24, 2018.

(51) Int. Cl.
| | | |
|---|---|---|
| C07K 16/28 | (2006.01) | |
| A61K 39/395 | (2006.01) | |
| A61K 47/68 | (2017.01) | |
| A61P 35/00 | (2006.01) | |
| A61P 35/02 | (2006.01) | |
| C07K 14/725 | (2006.01) | |
| C07K 16/46 | (2006.01) | |
| C07K 19/00 | (2006.01) | |
| C07K 14/705 | (2006.01) | |

(52) U.S. Cl.
CPC ...... *C07K 16/2878* (2013.01); *A61K 39/3955* (2013.01); *A61K 47/6849* (2017.08); *A61P 35/00* (2018.01); *A61P 35/02* (2018.01); *C07K 14/7051* (2013.01); *C07K 16/462* (2013.01); *C07K 19/00* (2013.01); *C07K 14/70578* (2013.01); *C07K 2317/24* (2013.01); *C07K 2317/41* (2013.01); *C07K 2317/51* (2013.01); *C07K 2317/54* (2013.01); *C07K 2317/55* (2013.01); *C07K 2317/565* (2013.01); *C07K 2317/622* (2013.01); *C07K 2317/76* (2013.01); *C07K 2319/02* (2013.01); *C07K 2319/03* (2013.01); *C07K 2319/30* (2013.01); *C07K 2319/33* (2013.01)

(58) Field of Classification Search
CPC ............ C07K 16/2878; A61K 39/3955
See application file for complete search history.

(56) References Cited

U.S. PATENT DOCUMENTS

| | | | |
|---|---|---|---|
| 7,090,843 B1 | 8/2006 | Francisco | |
| 7,446,190 B2 | 11/2008 | Sadelain | |
| 8,088,377 B2 | 1/2012 | Keler | |
| 11,584,799 B2* | 2/2023 | Medin | ..................... A61P 35/02 |
| 11,667,721 B2* | 6/2023 | Medin | ................ C07K 16/2809 |
| | | | 424/136.1 |
| 2013/0071414 A1 | 3/2013 | Dotti | |
| 2013/0287748 A1 | 10/2013 | June | |
| 2016/0200824 A1 | 7/2016 | Chmielewski | |
| 2020/0095330 A1 | 3/2020 | Medin et al. | |

FOREIGN PATENT DOCUMENTS

| | | |
|---|---|---|
| WO | 2003059282 A2 | 7/2003 |
| WO | 2014099671 A1 | 6/2014 |
| WO | 2016134284 A1 | 8/2016 |
| WO | 2017066122 A1 | 4/2017 |

OTHER PUBLICATIONS

European Patent Office, Communication Pursuant to Article 94(3) EPC, Application No. 19783839.4, Apr. 30, 2024, 5 pages.
ADC Review. Anonymous. Journal of Antibody-drug Conjugates: Monomethyl auristatin E (MMAE). Last updated Mar. 7, 2015.
Ahmed, N., et al. "HER2-specific T cells target primary glioblastoma stem cells and induce regression of autologous experimental tumors." Clinical Cancer Research 16.2 (2010): 474-485.
Altschul, S. F., et al. "Gapped BLAST and PSI-BLAST: a new generation of protein database search programs." Nucleic acids research 25.17 (1997): 3389-3402.
Batzer, M. A., et al. "Enhanced evolutionary PCR using oligonucleotides with inosine at the 3'-terminus." Nucleic acids research 19.18 (1991): 5081.
Brentjens, Re. J., et al. "Eradication of systemic B-cell tumors by genetically targeted human T lymphocytes co-stimulated by CD80 and interleukin-15." Nature medicine 9.3 (2003): 279-286.
Carde, P., et al. "Immunoscintigraphy of Hodgkin's disease: in vivo use of radiolabelled monoclonal antibodies derived from Hodgkin cell lines." European Journal of Cancer and Clinical Oncology 26.4 (1990): 474-479.
Chekmasova, A. A., et al. "Enhanced Antitumor Efficacy of MUC-16 Targeted T Cells Further Modified to Constitutively Express the IL-12 Cytokine in a Syngeneic Model of Ovarian Cancer." Blood. (2011): 4176-4176.
Chen, R et al. Five-year survival and durability results of brentuximab vedotin in patients with relapsed or refractory Hodgkin lymphoma. Blood. 2016 128:1562-1566.

(Continued)

*Primary Examiner* — Zachary C Howard
(74) *Attorney, Agent, or Firm* — Quarles & Brady LLP

(57) ABSTRACT

The present invention provides novel antibodies and antigen binding fragments thereof that bind to human CD30. Also presented are single chain variable antibodies, chimeric antigen receptors and uses thereof. Methods of treating cancer are also disclosed.

43 Claims, 14 Drawing Sheets
(13 of 14 Drawing Sheet(s) Filed in Color)
Specification includes a Sequence Listing.

(56) References Cited

OTHER PUBLICATIONS

Chiarle, R., et al. CD30 in normal and neoplastic cells. Clin. Immunol. 90(2):157-164 (1999).

Chicaybam, L. et al. "Chimeric antigen receptors in cancer immunogene therapy: current status and future directions." International reviews of immunology 30.5-6 (2011): 294-311.

Dabir, S., et al. CD30 is a potential therapeutic target in malignant mesothelioma. Molecular cancer therapeutics 14.3 (2015): 740-746.

Diamantis, N. et al. "Antibody-drug conjugates—an emerging class of cancer treatment." British journal of cancer 114.4 (2016): 362-367.

Friedrich, M et al. Preclinical characterization of AMG 330, a CD3/CD33-bispecific Tcell-engaging antibody with potential for treatment of acute myelogenous leukemia. Mol Cancer Ther. 2014 13(6):1549-57.

Froese, P., et al. "Biochemical characterization and biosynthesis of the Ki-1 antigen in Hodgkin-derived and virus-transformed human B and T lymphoid cell lines." The Journal of Immunology 139.6 (1987): 2081-2087.

Gaudio, F., et al. Outcome of very late relapse in patients with Hodgkin's lymphomas. Advances in hematology 2011 (2010).

Gopal, A. K., et al. High-dose therapy and autologous stem cell transplantation for chemoresistant Hodgkin lymphoma. Cancer 113.6 (2008): 1344-1350.

International Searching Authority, International Search Report and Written Opinion for application PCT/US2019/052618, mailed on Nov. 28, 2019.

Johnsson, B., et al. "Comparison of methods for immobilization to carboxymethyl dextran sensor surfaces by analysis of the specific activity of monoclonal antibodies." Journal of Molecular Recognition 8.1-2 (1995): 125-131.

Johnsson, B., et al. "Immobilization of proteins to a carboxymethyldextran-modified gold surface for biospecific interaction analysis in surface plasmon resonance sensors." Analytical biochemistry 198.2 (1991): 268-277.

Jönsson, U., et al. "Introducing a biosensor based technology for real-time biospecific interaction analysis." Annales de biologie clinique. vol. 51. No. 1. 1993. pp. 19-26.

Jonsson, U., et al. "Real-time biospecific interaction analysis using surface plasmon resonance and a sensor chip technology." Biotechniques 11.5 (1991): 620-627.

Karlin, S. et al. "Methods for assessing the statistical significance of molecular sequence features by using general scoring schemes." Proceedings of the National Academy of Sciences 87.6 (1990): 2264-2268.

Koon, H. B. et al. "Anti-CD30 antibody-based therapy." Current opinion in oncology 12.6 (2000): 588-593.

Kung Sutherland, MS et al. SGN-CD33A: a novel CD33-targeting antibody-drug conjugate using a pyrrolobenzodiazepine dimer is active in models of drug-resistant AML. Blood. 2013122(8):1455-1463.

Lum, L. G., et al. "Targeting T cells with bispecific antibodies for cancer therapy." BioDrugs 25.6 (2011): 365-379.

Lum, L. G., et al. "CD20-targeted T cells after stem cell transplantation for high risk and refractory non-Hodgkin's lymphoma." Biology of Blood and Marrow Transplantation 19.6 (2013): 925-933.

Ohtsuka, E., et al. "An alternative approach to deoxyoligonucleotides as hybridization probes by insertion of deoxyinosine at ambiguous codon positions." Journal of Biological Chemistry 260.5 (1985): 2605-2608.

Oldham, Raa, et al. Development of Novel alpha-CD30 CAR Immunotherapy for Hodgkin Lymphoma. Presented at the Fifth Annual Pediatric Cancer Symposium, Milwaukee, WI. May 10, 2018.

Rossolini, G. M. et al. "Use of deoxyinosine-containing primers vs degenerate primers for polymerase chain reaction based on ambiguous sequence information." Molecular and cellular probes 8.2 (1994): 91-98.

Sabattini E, et al. WHO classification of tumours of haematopoietic and lymphoid tissues in 2008: an overview. Pathologica 2010;102:83-7.

Sadelain, et al., "The Basic Principles of Chimeric Antigen Receptor Design." Cancer Discovery, OF1-11, (2013).

Safdari, Y, et al. "Antibody humanization methods—a review and update." Biotechnology and Genetic Engineering Reviews 29.2 (2013): 175-186.

Schwab, U, et al. "Production of a monoclonal antibody specific for Hodgkin and Sternberg—Reed cells of Hodgkin's disease and a subset of normal lymphoid cells." Nature 299.5878 (1982): 65-67.

Thakur, A. et al. "Cancer therapy with bispecific antibodies: Clinical experience." Current opinion in molecular therapeutics 12.3 (2010): 340.

Valton, J., et al. "A versatile safeguard for chimeric antigen receptor T-cell immunotherapies." Scientific reports 8.1 (2018): 1-8.

Verma, R., et al. "Antibody engineering: comparison of bacterial, yeast, insect and mammalian expression systems." Journal of immunological methods 216.1-2 (1998): 165-181.

Ward, E. S., et al. "Binding activities of a repertoire of single immunoglobulin variable domains secreted from *Escherichia coli*." Nature 341.6242 (1989): 544-546.

Wu C-Y, et al. ("Remote control of therapeutic T cells through a small molecule-gated chimeric receptor" Science 350 (6258), Oct. 16, 2015, aab4077-9.

Wu, X., et al. (2017). kpLogo: positional k-mer analysis reveals hidden specificity in biological sequences. Nucleic Acids Research. doi: 10.1093/nar/gkx323.

Younes, A et al. Results of a Pivotal Phase II Study of Brentuximab Vedotin for Patients with Relapsed or Refractory Hodgkin's Lymphoma. Journal of Clinical Oncology. 2012 30(18):2183-2189.

Zhong, X-S, et al. "Chimeric antigen receptors combining 4-1BB and CD28 signaling domains augment PI3kinase/AKT/Bcl-XL activation and CD8+ T cell-mediated tumor eradication." Molecular Therapy 18.2 (2010): 413-420.

Thakur, A. Optimize Synergistic Target Selection to Maximize Therapeutic Benefit. Presented at World Bispecific Conference. Sep. 30, 2016. Boston, MA USA.

Brudno, J., Kochenderfer, J. Chimeric antigen receptor T-cell therapies for lymphoma. Nat Rev Clin Oncol 15, 31-46 (2018). https://doi.org/10.1038/nrclinonc.2017.128.

\* cited by examiner

Light chain

|      | 8010 | 10c2 | 12B1 | 15B1 | 15B5 |
|------|------|------|------|------|------|
| 15B5 | 78%  | 52%  | 94%  | 56%  | ---  |
| 15B1 | 59%  | 54%  | 54%  | ---  |      |
| 12B1 | 73%  | 52%  | ---  |      |      |
| 10c2 | 55%  | ---  |      |      |      |
| 8010 | ---  |      |      |      |      |
| AG10 | 56%  | 60%  | 50%  | 59%  | 50%  |

FIG. 3A

Heavy chain

|      | 8010 | 10c2 | 12B1 | 15B1 | 15B5 |
|------|------|------|------|------|------|
| 15B5 | 85%  | 68%  | 90%  | 87%  | ---  |
| 15B1 | 90%  | 70%  | 86%  | ---  |      |
| 12B1 | 86%  | 73%  | ---  |      |      |
| 10c2 | 70%  | ---  |      |      |      |
| 8010 | ---  |      |      |      |      |
| AG10 | 72%  | 70%  | 72%  | 73%  | 70%  |

| Antibody | $K_A$ (M$^{-1}$) | $k_a$ (Ms$^{-1}$) | $K_D$ (nM) | $k_d$ (s$^{-1}$) |
|---|---|---|---|---|
| 8D10 | 16.9 x 10$^9$ | 10.1 x 10$^4$ | 0.0592 | 0.6 x 10$^{-5}$ |
| 10C2 | 1.65 x 10$^9$ | 30.7 x 10$^4$ | 0.607 | 18.6 x 10$^{-5}$ |
| 12B1 | 5.02 x 10$^9$ | 6.13 x 10$^4$ | 0.199 | 1.22 x 10$^{-5}$ |
| 13H1 | 6.7 x 10$^9$ | 70.8 x 10$^4$ | 0.149 | 10.6 x 10$^{-5}$ |
| 15B8 | 1.02 x 10$^9$ | 50.4 x 10$^4$ | 0.978 | 49.3 x 10$^{-5}$ |

B.

| Antibody | $K_A$ (M$^{-1}$) | $k_a$ (Ms$^{-1}$) | $K_D$ (nM) | $k_d$ (s$^{-1}$) |
|---|---|---|---|---|
| 8D10 | 8.78 x 10$^5$ | 4.53 x 10$^3$ | 1.14 | 5.23 x 10$^{-3}$ |
| 10C2 | 5.79 x 10$^5$ | 5.88 x 10$^3$ | 1.76 | 10.1 x 10$^{-3}$ |
| AC10 | 9.03 x 10$^7$ | 1.82 x 10$^5$ | 11.1nM | 2.02 x 10$^{-3}$ |

FIG. 16A

CD30 mAbs: scFv sequences

*Signal sequence*, Variable heavy chain, Linker, Variable light chain

>8D10.HL.scFv (SEQ ID NO: 41)

ATGGCCTTACCAGTGACCGCCTTGCTCCTGCCGCTGGCCTTGCTGCTCCACGCCGCCAGGCCG
CAAGTACAGCTGCAGGAGTCTGGGACTGAACTGGTGAAGCCTGGGGCTTCAGTGAAGCTGTCCTGCAAGGCTTCT
GGCTACACCTTCACCAGCTACTGGATGCACTGGATGAAGCAGAGGCCTGGACAAGGCCTTGAGTGGATTGGAAAT
ATTAATCCTAGCAATGGTGGTACTAACTACAATGAGAAGTTCAAGAACAAGGCCACACTGACTGTAGACAAATCC
TCCAGCACAGCCTACATGCAGCTCAGCAGCCTGACATCTGAGGACTCTGCGGTCTATTATTGTGCAAGAAGGGAT
TATTACTACGGTAGTAGCTACGGCTTCGATGTCTGGGGCACAGGGACCACGGTCACCGTCTCCTCAGGTGGCGGT
GGCTCGGGCGGTGGTGGGTCGGTGGCGGCGGATCTGATATTGTGATGACCCAGTCTCCTGCCTCCCAGTCTGCA
TCTCTGGGAGAAAGTGTCACCATCACATGCCTGGCAAGTCAGACCATTGGTACATGGTTAGCATGGTATCAGCAG
AAACCAGGGAAATCTCCTCAGTTCCTGATTTATGCTGCAACCAGCTTGGCAGATGGGGTCCCATCAAGGTTCAGT
GGTAGTGGATCTGGCACAAAATTTTCTTTCAAGATCAGCAGCCTACAGGCTGAAGATTTTGTAAGTTATTACTGT
CAACAACTTTACAGTACTCCGTTCACGTTCGGAGGGGGGACCAAGCTGGAAATAAAA

SEQ ID NO:42 (protein scFv_8D10)

MALPVTALLLPLALLLHAARPQVQLQESGTELVKPGASVKLSCKASGYTFTSYWM
HWMKQRPGQGLEWIGNINPSNGGTNYNEKFKNKATLTVDKSSSTAYMQLSSLTSE
DSAVYYCARRDYYYGSSYGFDVWGTGTTVTVSSGGGGSGGGGSGGGGSDIVMTQSP
ASQSASLGESVTITCLASQTIGTWLAWYQQKPGKSPQFLIYAATSLADGVPSRFSGS
GSGTKFSFKISSLQAEDFVSYYCQQLYSTPFTFGGGTKLEIK

SEQ ID NO: 43 (DNA scFv_8D10.LH.scFv)- (heavy and light chain switch order)

ATGGCCTTACCAGTGACCGCCTTGCTCCTGCCGCTGGCCTTGCTGCTCCACGCCGCCAGGCCG
GATATTGTGATGACCCAGTCTCCTGCCTCCCAGTCTGCATCTCTGGGAGAAAGTGTCACCATC
ACATGCCTGGCAAGTCAGACCATTGGTACATGGTTAGCATGGTATCAGCAGAAACCAGGGAA
ATCTCCTCAGTTCCTGATTTATGCTGCAACCAGCTTGGCAGATGGGGTCCCATCAAGGTTCAG
TGGTAGTGGATCTGGCACAAAATTTTCTTTCAAGATCAGCAGCCTACAGGCTGAAGATTTTG
TAAGTTATTACTGTCAACAACTTTACAGTACTCCGTTCACGTTCGGAGGGGGGACCAAGCTG
GAAATAAAAGGTGGCGGTGGCTCGGGCGGTGGTGGGTCGGTGGCGGCGGATCTCAAGTACA
GCTGCAGGAGTCTGGGACTGAACTGGTGAAGCCTGGGGCTTCAGTGAAGCTGTCCTGCAAGG
CTTCTGGCTACACCTTCACCAGCTACTGGATGCACTGGATGAAGCAGAGGCCTGGACAAGGCC
TTGAGTGGATTGGAAATATTAATCCTAGCAATGGTGGTACTAACTACAATGAGAAGTTCAAG
AACAAGGCCACACTGACTGTAGACAAATCCTCCAGCACAGCCTACATGCAGCTCAGCAGCCTG
ACATCTGAGGACTCTGCGGTCTATTATTGTGCAAGAAGGGATTATTACTACGGTAGTAGCTA
CGGCTTCGATGTCTGGGGCACAGGGACCACGGTCACCGTCTCCTCA

SEQ ID NO: 44 (Protein scFv_8D10.LH.scFv)- (heavy and light chain switch order)

MALPVTALLLPLALLLHAARPDIVMTQSPASQSASLGESVTITCLAS
QTIGTWLAWYQQKPGKSPQFLIYAATSLADGVPSRFSGSGSGTKFSF
KISSLQAEDFVSYYCQQLYSTPFTFGGGTKLEIKGGGGSGGGGSGGGG
SQVQLQESGTELVKPGASVKLSCKASGYTFTSYWMHWMKQRPGQG
LEWIGNINPSNGGTNYNEKFKNKATLTVDKSSSTAYMQLSSLTSEDS
AVYYCARRDYYYGSSYGFDVWGTGTTVTVSS

FIG. 16B

SEQ ID NO: 45 (DNA scFv_10C2.HL.scFv)

ATGGCCTTACCAGTGACCGCCTTGCTCCTGCCGCTGGCCTTGCTGCTCCACGCCGCCAGGCCG
CAGGTGCAGCTGGAGCAGTCTGGACCTGTGCTGGTGAAGCCTGGGGCTTCAGTGAAGATGTCCTGTAAGGCTTCT
GGATACACATTCACTGACTACTATATGAACTGGGTGAAGCAGAGCCATGGAAAGAGCCTTGAGTGGATTGGAGT
TATTAATCCTTACAACGGTGGTACTAGCTACAACCAGAAGTTCAAGGGCAAGGCCACATTGACTGTTGACAAGTC
CTCCAGCACAGCCTGCATGGAGCTCAACTGCCTAACATCTGAGGACTCTGCAGTCTATTACTGTACCCTGGGGGCT
TACTGGGGTCAAGGAACCTCAGTCACCGTCTCCTCAGGTGGCGGTGGCTCGGGCGGTGGTGGGTCGGGTGGCGGC
GGATCTGATATTGTGCTGACACAGACTCCACTCACTTTGTCGGTTACCATTGGACAACCAGCCTCCATCTCTTGCA
AGTCAAATCAGAGCCTCTTAGATAGTTATGGAAAGACATATTTGAATTGGTTGTTACAGAGGCCAGGCCAGTCTC
CAAAGCGCCTAATCTATCTGGTGTCTAAACTGGACTCTGGAGTCCCTGACAGGTTCACTGGCAGTGGATCAGGGA
CAGATTTCACACTGAAAATCAGCAGAGTGGAGGCTGAGGATTTGGGAGTTTATTATTGCTGGCAAGGTACACAT
TTTCCTCGGACGTTCGGTGGAGGCACCAAGCTGGAAATCAAA

SEQ ID NO: 46 (Protein scFv_10C2.HL.scFv)

M A L P V T A L L L P L A L L L H A A R P Q V Q L E Q S G P V L V K P G A S V K M S C K A S
G Y T F T D Y Y M N W V K Q S H G K S L E W I G V I N P Y N G G T S Y N Q K F K G K A T L T
V D K S S S T A C M E L N C L T S E D S A V Y Y C T L G A Y W G Q G T S V T V S S G G G G S
G G G G S G G G G S D I V L T Q T P L T L S V T I G Q P A S I S C K S N Q S L L D S Y G K T Y L
N W L L Q R P G Q S P K R L I Y L V S K L D S G V P D R F T G S G S G T D F T L K I S R V E A
E D L G V Y Y C W Q G T H F P R T F G G G T K L E I K

SEQ ID NO: 47 (DNA scFv_12B1.HL.scFv)

ATGGCCTTACCAGTGACCGCCTTGCTCCTGCCGCTGGCCTTGCTGCTCCACGCCGCCAGGCCG
GAGGTCAAGCTGGAGGAGTCAGGGACTGAACTGGTGAAGCCTGGGGCTTCAGTGAAGCTGTCCTGCAAGGCTTCT
GGCTACACCTTCACCAGCTACTGGATGCACTGGGTGAAGCAGAGGCCTGGACAAGGCCTTGAGTGGATTGGAAAT
ATTAATCCTACCAATGGTGGTACTAACTACAATGAGAAGTTCAAGAGCAAGGCCACACTGACTGTAGACAAATCC
TCCAGAACAGCCTACATGCAGCTCAGCAGCCTGACATCTGGGGACTCAGCGGTCTACTATTGTGCAAGAAGGGAC
TTTATTACTACATCCGGGTTTGCTTACTGGGGCCAAGGGACTCTGGTCACTGTCTCTGCAGGTGGCGGTGGCTCG
GGCGGTGGTGGGTCGGGTGGCGGCGGATCTGATATTGTGATGACACAGACTACAGCCTCCCTATCTACATCTGTG
GGAGAAACTGTCACCATCACATGTCGAGCAAGTGGGAATCTTCACAGTTATTTAACATGGTATCAGCAGAAACAG
GGAAAGTCTCCTCAGCTCCTGGTCTATAATGCAAAAACCTTAGCAGATGGTGTGCCATCAAGGTTCAGTGGCAGT
GGATCAGGAACACAATATTCTCTCAAGATCGACAGCCTGCAGCCTGAAGATTTTGGGAGTTATTACTGTCAACAT
TTTTGGACTACTCCATTCACGTTCGGCTCGGGGACAAAGTTGGAGATAAAAC

SEQ ID NO: 48 (Protein scFv_12B1.HL.scFv)

M A L P V T A L L L P L A L L L H A A R P E V K L E E S G T E L V K P G A S V K L S C K A S G Y T F T S Y W M H
W V K Q R P G Q G L E W I G N I N P T N G G T N Y N E K F K S K A T L T V D K S S R T A Y M Q L S S L T S G D
S A V Y Y C A R R D F I T T S G F A Y W G Q G T L V T V S A G G G G S G G G G S G G G G S D I V M T Q T T A S L
S T S V G E T V T I T C R A S G N L H S Y L T W Y Q Q K Q G K S P Q L L V Y N A K T L A D G V P S R F S G S G S
G T Q Y S L K I D S L Q P E D F G S Y Y C Q H F W T T P F T F G S G T K L E I K

SEQ ID NO: 49 (DNA scFv_13H1.HL.scFv)

ATGGCCTTACCAGTGACCGCCTTGCTCCTGCCGCTGGCCTTGCTGCTCCACGCCGCCAGGCCG
CAAGTCCAGCTGCAGCAGTCTGGGACTGAACTGGTGAAGCCTGGGGCTTCAGTGAAGCTGTCCTGCAAGGCTTCT
GGCCACACCTTCACCAGCTACTGGATGCACTGGGTGAAGCAGAGGCCTGGACAAGGCCTTGAGTGGATTGGAAAT
ATTAATCCTAGCAATGGTGGTACTAACTACAATGAGAAGTTCAAGAGCAAGGCCACACTGACTGTAGACAAATCC
TCCAGCACAGCCTACATGCAGCTCAGCAGCCTGACATCTGAGGACTCTGCGGTCTATTATTGTGCAAGAAGGGGA
TACTACGGTAGTAGCAGCTACTGGTCCTTCGATGTCTGGGGCACAGGGACCACGGTCACCGTCTCCTCAGGTGGC
GGTGGCTCGGGCGGTGGTGGGTCGGGTGGCGGCGGATCTGACATTGTGATGACCCAGACTCCCAAATCCATGTCC
ATGTCAGTAGGAGAGAGGGTCACCTTGAGCTGCAAGGCCAGTGAGAATGTGGGTACTTATGTATCCTGGTATCAA
CAGAAACCAGAGCAGTCTCCTAAAGTGCTGATATACGGGGCATCCAACCGGTTCACTGGGGTCCCCGATCGCTTC
ACAGGCAGTGGATCTGCAACAGATTTCACTCTGACCATCAGTAGTGTGCAGACTGAGGACCTTGCAGATTATCAC
TGTGGACAGAGTTACAGCTATCCGCTCACGTTCGGTGCTGGGACCAAGCTGGAGCTGAAAC

FIG. 16C

SEQ ID NO: 50 (Protein scFv_13H1.HL.scFv)

MALPVTALLLPLALLLHAARPQVQLQQSGTELVKPGASVKLSCKASGHTFTSYWM
HWVKQRPGQGLEWIGNINPSNGGTNYNEKFKSKATLTVDKSSSTAYMQLSSLTSE
DSAVYYCARRGYYGSSSYWSFDVWGTGTTVTVSSGGGGSGGGGSGGGGSDIVMTQ
TPKSMSMSVGERVTLSCKASENVGTYVSWYQQKPEQSPKVLIYGASNRFTGVPDR
FTGSGSATDFTLTISSVQTEDLADYHCGQSYSYPLTFGAGTKLELK

SEQ ID NO: 51 (DNA-scFv_15B8.HL.scFv)

ATGGCCTTACCAGTGACCGCCTTGCTCCTGCCGCTGGCCTTGCTGCTCCACGCCGCCAGGCCGCAGGTTCAGCTGG
AGCAGTCTGGGACTGAACTGGTGAAGCCTGGGGCTTCAGTGAAGCTGTCCTGCAAGGCTTCTGGCTACACCTTCA
CCAGCTACTGGATGCACTGGGTGAAGCAGAGGCCTGGACAAGGCCTTGAGTGGATTGGAAATATTAATCCTAGCA
ATGGTGGTACTAACTACAATGAGAAGTTCAAGAGCAAGGCCACACTGACTGTAGACAAATCCTCCAGCACAGCCT
ACATGCAGCTCAGCAGCCTGACATCTGAGGACTCTGCGATCTATTATTGTGCAAGACGGAATAATTACTACGCTA
GTAGCCCTTTTGCTTACTGGGGCCAAGGGACTCTGGTCAGTGTCTCTGCAGGTGGCGGTGGCTCGGGCGGTGGTG
GGTCGGGTGGCGGCGGATCTGACATTGTGATGACACAGACTCCAGCCTCCCTATCTGCATCTGTGGGAGAAACTG
TCACCATCACATGTCGAGCAAGTGGGAATATTCACAATTATTTAGCATGGTATCAGCAGAAACAGGGAAAATCTC
CTCAGCTCCTGGTCTATAATGCAAAAACCTTAGCAGATGGTGTGCCATCAAGGTTCAGTGGCAGTGGATCAGGAA
CACAATATTCTCTCAAGATCAACAGCCTGCAGCCTGAAGATTTTGGGAGTTATTACTGTCAACATTTTTGGAGTA
CTCCATTCACGTTCGGCTCGGGGACAAAGTTGGAAATAAAAC

SEQ ID NO: 52 (Protein scFv_15B8.HL.scFv)

MALPVTALLLPLALLLHAARPQVQLEQSGTELVKPGASVKLSCKASGYTFTSYWM
HWVKQRPGQGLEWIGNINPSNGGTNYNEKFKSKATLTVDKSSSTAYMQLSSLTSE
DSAIYYCARRNNYYASSPFAYWGQGTLVSVSAGGGGSGGGGSGGGGSDIVMTQTPA
SLSASVGETVTITCRASGNIHNYLAWYQQKQGKSPQLLVYNAKTLADGVPSRFSGS
GSGTQYSLKINSLQPEDFGSYYCQHFWSTPFTFGSGTKLEIK

CD30: CAR sequences

Our CD30 CARs may use any of the scFv sequences listed above, in HL or LH format. An exemplary 8D10.HL.CAR is shown below. We typically use a CD8 hinge and transmembrane domain, and a 4-1BB co-stimulatory domain, but these elements may be swapped out for other commonly used CAR components, such as an IgG4 hinge domain, or a CD28 co-stimulatory domain.
Legend- Signal sequence, Variable heavy chain, Linker, Variable light chain, CD8 hinge, CD8 transmembrane domain, 41BB costimulatory domain, CD3ζ intracellular signaling domain, STOP

FIG. 16D

SEQ ID NO: 53 (DNA scFv_8D10.HL.CAR)

ATGGCCTTACCAGTGACCGCCTTGCTCCTGCCGCTGGCCTTGCTGCTCCACGCCGCCAGGCCG
CAAGTACAGCTGCAGGAGTCTGGGACTGAACTGGTGAAGCCTGGGGCTTCAGTGAAGCTGTCCT
GCAAGGCTTCTGGCTACACCTTCACCAGCTACTGGATGCACTGGATGAAGCAGAGGCCTGGACA
AGGCCTTGAGTGGATTGGAAATATTAATCCTAGCAATGGTGGTACTAACTACAATGAGAAGTTCA
AGAACAAGGCCACACTGACTGTAGACAAATCCTCCAGCACAGCCTACATGCAGCTCAGCAGCCT
GACATCTGAGGACTCTGCGGTCTATTATTGTGCAAGAAGGGATTATTACGGTAGTAGCTACG
GCTTCGATGTCTGGGGCACAGGGACCACGGTCACCGTCTCCTCAGGTGGCGGTGGCTCGGGC
GGTGGTGGGTCGGGTGGCGGCGGATCTGATATTGTGATGACCCAGTCTCCTGCCTCCCAGTCT
GCATCTCTGGGAGAAAGTGTCACCATCACATGCCTGGCAAGTCAGACCATTGGTACATGGTTAG
CATGGTATCAGCAGAAACCAGGGAAATCTCCTCAGTTCCTGATTTATGCTGCAACCAGCTTGGCA
GATGGGGTCCCATCAAGGTTCAGTGGTAGTGGATCTGGCACAAAATTTTCTTTCAAGATCAGCAG
CCTACAGGCTGAAGATTTTGTAAGTTATTACTGTCAACAACTTTACAGTACTCCGTTCACGTTCGG
AGGGGGGACCAAGCTGGAAATAAAAACCACGACGCCAGCGCCGCGACCACCAACACCGGCGC
CCACCATCGCGTCGCAGCCCCTGTCCCTGCGCCCAGAGGCGTGCCGGCCAGCGGCGGGGGG
GCAGTGCACACGAGGGGGCTGGACTTCGCCTGTGATATCTACATCTGGGCGCCCTTGGCCGGG
ACTTGTGGGGTCCTTCTCCTGTCACTGGTTATCACCCTTTACTGCAAACGGGGCAGAAAGAAACT
CCTGTATATATTCAAACAACCATTTATGAGACCAGTACAAACTACTCAAGAGGAAGATGGCTGTA
GCTGCCGATTTCCAGAAGAAGAAGAAGGAGGATGTGAACTGAGAGTGAAGTTCAGCAGGAGCG
CAGACGCCCCCGCGTACAAGCAGGGCCAGAACCAGCTCTATAACGAGCTCAATCTAGGACGAA
GAGAGGAGTACGATGTTTTGGACAAGAGACGTGGCCGGGACCCTGAGATGGGGGGAAAGCCGA
GAAGGAAGAACCCTCAGGAAGGCCTGTACAATGAACTGCAGAAAGATAAGATGGCGGAGGCCTA
CAGTGAGATTGGGATGAAAGGCGAGCGCCGGAGGGGCAAGGGGCACGATGGCCTTTACCAGG
GTCTCAGTACAGCCACCAAGGACACCTACGACGCCCTTCACATGCAGGCCCTGCCCCCTCGC**TA
G**

SEQ ID NO: 54 (Protein scFv_8D10.HL.CAR)

MALPVTALLLPLALLHAARPQVQLQESGTELVKPGASVKLSCKASGY
TFTSYWMHWMKQRPGQGLEWIGNINPSNGGTNYNEKFKNKATLTVD
KSSSTAYMQLSSLTSEDSAVYYCARRDYYYGSSYGFDVWGTGTTVTV
SSGGGGSGGGGSGGGGSDIVMTQSPASQSASLGESVTITCLASQTIG
TWLAWYQQKPGKSPQFLIYAATSLADGVPSRFSGSGSGTKFSFKISSL
QAEDFVSYYCQQLYSTPFTFGGGTKLEIKTTTPAPRPPTPAPTIASQP
LSLRPEACRPAAGGAVHTRGLDFACDIYIWAPLAGTCGVLLLSLVITLY
CKRGRKKLLYIFKQPFMRPVQTTQEEDGCSCRFPEEEEGGCELRVKF
SRSADAPAYKQGQNQLYNELNLGRREEYDVLDKRRGRDPEMGGKPR
RKNPQEGLYNELQKDKMAEAYSEIGMKGERRRGKHDGLYQGLSTAT
KDTYDALHMQALPPR

SEQ ID NO:55 (DNA-sequence to link after the scFv listed above)

ACCACGACGCCAGCGCCGCGACCACCAACACCGGCGCCCACCATCGCGTCGCAGCCCCTGTC
CCTGCGCCCAGAGGCGTGCCGGCCAGCGGCGGGGGGCAGTGCACACGAGGGGCTGGAC
TTCGCCTGTGATATCTACATCTGGGCGCCCTTGGCCGGGACTTGTGGGGTCCTTCTCCTGTCAC
TGGTTATCACCCTTTACTGCAAACGGGGCAGAAAGAAACTCCTGTATATATTCAAACAACCATTTA
TGAGACCAGTACAAACTACTCAAGAGGAAGATGGCTGTAGCTGCCGATTTCCAGAAGAAGAAGA
AGGAGGATGTGAACTGAGAGTGAAGTTCAGCAGGAGCGCAGACGCCCCCGCGTACAAGCAGGG
CCAGAACCAGCTCTATAACGAGCTCAATCTAGGACGAAGAGAGGAGTACGATGTTTTGGACAAG
AGACGTGGCCGGGACCCTGAGATGGGGGGAAAGCCGAGAAGGAAGAACCCTCAGGAAGGCCT
GTACAATGAACTGCAGAAAGATAAGATGGCGGAGGCCTACAGTGAGATTGGGATGAAAGGCGAG
CGCCGGAGGGGCAAGGGGCACGATGGCCTTTACCAGGGTCTCAGTACAGCCACCAAGGACACC
TACGACGCCCTTCACATGCAGGCCCTGCCCCCTCGCTAG

SEQ ID NO:56- Protein sequence of CAR to link to ScFv via linker

TTTPAPRPPTPAPTIASQPLSLRPEACRPAAGGAVHTRGLDFACDIYI
WAPLAGTCGVLLLSLVITLYCKRGRKKLLYIFKQPFMRPVQTTQEEDG
CSCRFPEEEEGGCELRVKFSRSADAPAYKQGQNQLYNELNLGRREEY
DVLDKRRGRDPEMGGKPRRKNPQEGLYNELQKDKMAEAYSEIGMKG
ERRRGKHDGLYQGLSTATKDTYDALHMQALPPR

SEQUENCE LISTING

```
Sequence total quantity: 56
SEQ ID NO: 1                 moltype = AA  length = 107
FEATURE                      Location/Qualifiers
REGION                       1..107
                             note = synthetic - 8D10 light chain
source                       1..107
                             mol_type = protein
                             organism = synthetic construct
SEQUENCE: 1
DIVMTQSPAS QSASLGESVT ITCLASQTIG TWLAWYQQKP GKSPQFLIYA ATSLADGVPS   60
RFSGSGSGTK FSFKISSLQA EDFVSYYCQQ LYSTPFTFGG GTKLEIK                107

SEQ ID NO: 2                 moltype = AA  length = 11
FEATURE                      Location/Qualifiers
REGION                       1..11
                             note = synthetic - CDRL1
source                       1..11
                             mol_type = protein
                             organism = synthetic construct
SEQUENCE: 2
LASQTIGTWL A                                                        11

SEQ ID NO: 3                 moltype = AA  length = 7
FEATURE                      Location/Qualifiers
REGION                       1..7
                             note = synthetic - CDRL2
source                       1..7
                             mol_type = protein
                             organism = synthetic construct
SEQUENCE: 3
AATSLAD                                                             7

SEQ ID NO: 4                 moltype = AA  length = 9
FEATURE                      Location/Qualifiers
REGION                       1..9
                             note = synthetic - CDRL3
source                       1..9
                             mol_type = protein
                             organism = synthetic construct
SEQUENCE: 4
QQLYSTPFT                                                           9

SEQ ID NO: 5                 moltype = AA  length = 122
FEATURE                      Location/Qualifiers
REGION                       1..122
                             note = synthetic - 8D10 heavy chain
source                       1..122
                             mol_type = protein
                             organism = synthetic construct
SEQUENCE: 5
QVQLQESGTE LVKPGASVKL SCKASGYTFT SYWMHWMKQR PGQGLEWIGN INPSNGGTNY   60
NEKFKNKATL TVDKSSSTAY MQLSSLTSED SAVYYCARRD YYYGSSYGFD VWGTGTTVTV  120
SS                                                                 122

SEQ ID NO: 6                 moltype = AA  length = 7
FEATURE                      Location/Qualifiers
REGION                       1..7
                             note = synthetic - CDH1
source                       1..7
                             mol_type = protein
                             organism = synthetic construct
SEQUENCE: 6
GYTFTSY                                                             7

SEQ ID NO: 7                 moltype = AA  length = 6
FEATURE                      Location/Qualifiers
REGION                       1..6
                             note = synthetic - CDH2
source                       1..6
                             mol_type = protein
                             organism = synthetic construct
SEQUENCE: 7
NPSNGG                                                              6

SEQ ID NO: 8                 moltype = AA  length = 13
FEATURE                      Location/Qualifiers
REGION                       1..13
                             note = synthetic - CDH3
```

```
source                  1..13
                        mol_type = protein
                        organism = synthetic construct
SEQUENCE: 8
RDYYYGSSYG FDV                                                          13

SEQ ID NO: 9            moltype = AA  length = 112
FEATURE                 Location/Qualifiers
REGION                  1..112
                        note = synthetic - 10C2 light chain
source                  1..112
                        mol_type = protein
                        organism = synthetic construct
SEQUENCE: 9
DIVLTQTPLT LSVTIGQPAS ISCKSNQSLL DSYGKTYLNW LLQRPGQSPK RLIYLVSKLD        60
SGVPDRFTGS GSGTDFTLKI SRVEAEDLGV YYCWQGTHFP RTFGGGTKLE IK                112

SEQ ID NO: 10           moltype = AA  length = 16
FEATURE                 Location/Qualifiers
REGION                  1..16
                        note = synthetic - CDRL1
source                  1..16
                        mol_type = protein
                        organism = synthetic construct
SEQUENCE: 10
KSNQSLLDSY GKTYLN                                                       16

SEQ ID NO: 11           moltype = AA  length = 7
FEATURE                 Location/Qualifiers
REGION                  1..7
                        note = synthetic - CDRL2
source                  1..7
                        mol_type = protein
                        organism = synthetic construct
SEQUENCE: 11
LVSKLDS                                                                 7

SEQ ID NO: 12           moltype = AA  length = 9
FEATURE                 Location/Qualifiers
REGION                  1..9
                        note = synthetic - CDRL3
source                  1..9
                        mol_type = protein
                        organism = synthetic construct
SEQUENCE: 12
WQGTHFPRT                                                               9

SEQ ID NO: 13           moltype = AA  length = 112
FEATURE                 Location/Qualifiers
REGION                  1..112
                        note = synthetic - 10C2 heavy chain
source                  1..112
                        mol_type = protein
                        organism = synthetic construct
SEQUENCE: 13
QVQLEQSGPV LVKPGASVKM SCKASGYTFT DYYMNWVKQS HGKSLEWIGV INPYNGGTSY        60
NQKFKGKATL TVDKSSSTAC MELNCLTSED SAVYYCTLGA YWGQGTSVTV SS                112

SEQ ID NO: 14           moltype = AA  length = 7
FEATURE                 Location/Qualifiers
REGION                  1..7
                        note = synthetic - CDH1
source                  1..7
                        mol_type = protein
                        organism = synthetic construct
SEQUENCE: 14
GYTFTDY                                                                 7

SEQ ID NO: 15           moltype = AA  length = 5
FEATURE                 Location/Qualifiers
REGION                  1..5
                        note = synthetic - CDH2
source                  1..5
                        mol_type = protein
                        organism = synthetic construct
SEQUENCE: 15
NPYNG                                                                   5

SEQ ID NO: 16           moltype =     length =
```

```
SEQUENCE: 16
000

SEQ ID NO: 17           moltype = AA  length = 107
FEATURE                 Location/Qualifiers
REGION                  1..107
                        note = synthetic - 12B1 light chain
source                  1..107
                        mol_type = protein
                        organism = synthetic construct
SEQUENCE: 17
DIVMTQTTAS LSTSVGETVT ITCRASGNLH SYLTWYQQKQ GKSPQLLVYN AKTLADGVPS    60
RFSGSGSGTQ YSLKIDSLQP EDFGSYYCQH FWTTPFTFGS GTKLEIK                 107

SEQ ID NO: 18           moltype = AA  length = 11
FEATURE                 Location/Qualifiers
REGION                  1..11
                        note = synthetic - CDRL1
source                  1..11
                        mol_type = protein
                        organism = synthetic construct
SEQUENCE: 18
RASGNLHSYL T                                                         11

SEQ ID NO: 19           moltype = AA  length = 7
FEATURE                 Location/Qualifiers
REGION                  1..7
                        note = synthetic - CDRL2
source                  1..7
                        mol_type = protein
                        organism = synthetic construct
SEQUENCE: 19
NAKTLAD                                                              7

SEQ ID NO: 20           moltype = AA  length = 9
FEATURE                 Location/Qualifiers
REGION                  1..9
                        note = synthetic - CDRL3
source                  1..9
                        mol_type = protein
                        organism = synthetic construct
SEQUENCE: 20
QHFWTTPFT                                                            9

SEQ ID NO: 21           moltype = AA  length = 120
FEATURE                 Location/Qualifiers
REGION                  1..120
                        note = synthetic - 12B1 heavy chain
source                  1..120
                        mol_type = protein
                        organism = synthetic construct
SEQUENCE: 21
EVKLEESGTE LVKPGASVKL SCKASGYTFT SYWMHWVKQR PGQGLEWIGN INPTNGGTNY    60
NEKFKSKATL TVDKSSRTAY MQLSSLTSGD SAVYYCARRD FITTSGFAYW GQGTLVTVSA   120

SEQ ID NO: 22           moltype = AA  length = 7
FEATURE                 Location/Qualifiers
REGION                  1..7
                        note = synthetic - CDH1
source                  1..7
                        mol_type = protein
                        organism = synthetic construct
SEQUENCE: 22
GYTFTSY                                                              7

SEQ ID NO: 23           moltype = AA  length = 6
FEATURE                 Location/Qualifiers
REGION                  1..6
                        note = synthetic - CDH2
source                  1..6
                        mol_type = protein
                        organism = synthetic construct
SEQUENCE: 23
NPTNGG                                                               6

SEQ ID NO: 24           moltype = AA  length = 11
FEATURE                 Location/Qualifiers
REGION                  1..11
                        note = synthetic - CDH3
```

```
source                   1..11
                         mol_type = protein
                         organism = synthetic construct
SEQUENCE: 24
RDFITTSGFA Y                                                                        11

SEQ ID NO: 25            moltype = AA  length = 107
FEATURE                  Location/Qualifiers
REGION                   1..107
                         note = synthetic - 13H1 light chain
source                   1..107
                         mol_type = protein
                         organism = synthetic construct
SEQUENCE: 25
DIVMTQTPKS MSMSVGERVT LSCKASENVG TYVSWYQQKP EQSPKVLIYG ASNRFTGVPD                    60
RFTGSGSATD FTLTISSVQT EDLADYHCGQ SYSYPLTFGA GTKLELK                                  107

SEQ ID NO: 26            moltype = AA  length = 11
FEATURE                  Location/Qualifiers
REGION                   1..11
                         note = synthetic - CDRL1
source                   1..11
                         mol_type = protein
                         organism = synthetic construct
SEQUENCE: 26
KASENVGTYV S                                                                        11

SEQ ID NO: 27            moltype = AA  length = 7
FEATURE                  Location/Qualifiers
REGION                   1..7
                         note = synthetic - CDRL2
source                   1..7
                         mol_type = protein
                         organism = synthetic construct
SEQUENCE: 27
GASNRFT                                                                             7

SEQ ID NO: 28            moltype = AA  length = 9
FEATURE                  Location/Qualifiers
REGION                   1..9
                         note = synthetic - CDRL3
source                   1..9
                         mol_type = protein
                         organism = synthetic construct
SEQUENCE: 28
GQSYSYPLT                                                                           9

SEQ ID NO: 29            moltype = AA  length = 123
FEATURE                  Location/Qualifiers
REGION                   1..123
                         note = synthetic - 13H1 heavy chain
source                   1..123
                         mol_type = protein
                         organism = synthetic construct
SEQUENCE: 29
QVQLQQSGTE LVKPGASVKL SCKASGHTFT SYWMHWVKQR PGQGLEWIGN INPSNGGTNY                    60
NEKFKSKATL TVDKSSSTAY MQLSSLTSED SAVYYCARRG YYGSSSYWSF DVWGTGTTVT                    120
VSS                                                                                 123

SEQ ID NO: 30            moltype = AA  length = 7
FEATURE                  Location/Qualifiers
REGION                   1..7
                         note = synthetic - CDH1
source                   1..7
                         mol_type = protein
                         organism = synthetic construct
SEQUENCE: 30
GHTFTSY                                                                             7

SEQ ID NO: 31            moltype = AA  length = 6
FEATURE                  Location/Qualifiers
REGION                   1..6
                         note = synthetic - CDH2
source                   1..6
                         mol_type = protein
                         organism = synthetic construct
SEQUENCE: 31
NPSNGG                                                                              6
```

```
SEQ ID NO: 32              moltype = AA   length = 14
FEATURE                    Location/Qualifiers
REGION                     1..14
                           note = synthetic - CDH3
source                     1..14
                           mol_type = protein
                           organism = synthetic construct
SEQUENCE: 32
RGYYGSSSYW SFDV                                                          14

SEQ ID NO: 33              moltype = AA   length = 107
FEATURE                    Location/Qualifiers
REGION                     1..107
                           note = synthetic - 15B8 light chain
source                     1..107
                           mol_type = protein
                           organism = synthetic construct
SEQUENCE: 33
DIVMTQTPAS LSASVGETVT ITCRASGNIH NYLAWYQQKQ GKSPQLLVYN AKTLADGVPS         60
RFSGSGSGTQ YSLKINSLQP EDFGSYYCQH FWSTPFTFGS GTKLEIK                      107

SEQ ID NO: 34              moltype = AA   length = 11
FEATURE                    Location/Qualifiers
REGION                     1..11
                           note = synthetic - CDRL1
source                     1..11
                           mol_type = protein
                           organism = synthetic construct
SEQUENCE: 34
RASGNIHNYL A                                                             11

SEQ ID NO: 35              moltype = AA   length = 7
FEATURE                    Location/Qualifiers
REGION                     1..7
                           note = synthetic - CDRL2
source                     1..7
                           mol_type = protein
                           organism = synthetic construct
SEQUENCE: 35
NAKTLAD                                                                  7

SEQ ID NO: 36              moltype = AA   length = 9
FEATURE                    Location/Qualifiers
REGION                     1..9
                           note = synthetic - CDRL3
source                     1..9
                           mol_type = protein
                           organism = synthetic construct
SEQUENCE: 36
QHFWSTPFT                                                                9

SEQ ID NO: 37              moltype = AA   length = 121
FEATURE                    Location/Qualifiers
REGION                     1..121
                           note = synthetic - 15B8 heavy chain
source                     1..121
                           mol_type = protein
                           organism = synthetic construct
SEQUENCE: 37
QVQLEQSGTE LVKPGASVKL SCKASGYTFT SYWMHWVKQR PGQGLEWIGN INPSNGGTNY         60
NEKFKSKATL TVDKSSSTAY MQLSSLTSED SAIYYCARRN NYYASSPPAY WGQGTLVSVS         120
A                                                                        121

SEQ ID NO: 38              moltype = AA   length = 7
FEATURE                    Location/Qualifiers
REGION                     1..7
                           note = synthetic - CDH1
source                     1..7
                           mol_type = protein
                           organism = synthetic construct
SEQUENCE: 38
GYTFTSY                                                                  7

SEQ ID NO: 39              moltype = AA   length = 6
FEATURE                    Location/Qualifiers
REGION                     1..6
                           note = synthetic - CDH2
source                     1..6
                           mol_type = protein
```

```
                            organism = synthetic construct
SEQUENCE: 39
NPSNGG                                                                          6

SEQ ID NO: 40               moltype = AA   length = 12
FEATURE                     Location/Qualifiers
REGION                      1..12
                            note = synthetic - CDH3
source                      1..12
                            mol_type = protein
                            organism = synthetic construct
SEQUENCE: 40
RNNYYASSPF AY                                                                  12

SEQ ID NO: 41               moltype = DNA   length = 795
FEATURE                     Location/Qualifiers
misc_feature                1..795
                            note = synthetic - 8D10
source                      1..795
                            mol_type = other DNA
                            organism = synthetic construct
SEQUENCE: 41
atggccttac cagtgaccgc cttgctcctg ccgctggcct tgctgctcca cgccgccagg              60
ccgcaagtac agctgcagga gtctgggact gaactggtga agcctggggc ttcagtgaag             120
ctgtcctgca aggcttctgg ctacaccttc accagctact ggatgcactg gatgaagcag             180
aggcctggac aaggccttga gtggattgga aatattatcc ctagcaatgg tggtactaac             240
tacaatgaga agttcaagaa caaggccaca ctgactgtag acaaatcctc cagcacagcc             300
tacatgcagc tcagcagcct gacatctgag gactctgcgg tctattattg tgcaagaagg             360
gattattact acggtagtag ctacggcttc gatgtctggg gcacagggac cacggtcacc             420
gtctcctcag gtggcggtgg ctcgggcggt ggtgggtcgg gtggcggctc atctgatatt             480
gtgatgaccc agtctccctg ctcccagtct gcatctctgg gagaaagtgt caccatcaca             540
tgcctggcaa gtcagaccat tggtacatgg ttagcatggt atcagcagaa accagggaaa             600
tctcctcagt tcctgattta tgctgcaacc agcttggcag atggggtccc atcaaggttc             660
agtggtagtg gatctggcac aaaatttttc ttcaagatca gcagcctaca ggctgaagat             720
tttgtaagtt attactgtca acaactttac agtactccgt tcacgttcgg agggggggacc            780
aagctggaaa taaaa                                                              795

SEQ ID NO: 42               moltype = AA   length = 265
FEATURE                     Location/Qualifiers
REGION                      1..265
                            note = synthetic - 8D10
source                      1..265
                            mol_type = protein
                            organism = synthetic construct
SEQUENCE: 42
MALPVTALLL PLALLLHAAR PQVQLQESGT ELVKPGASVK LSCKASGYTF TSYWMHWMKQ              60
RPGQGLEWIG NINPSNGGTN YNEKFKNKAT LTVDKSSSTA YMQLSSLTSE DSAVYYCARR             120
DYYYGSSYGF DVWGTGTTVT VSSGGGGSGG GGSGGGGSDI VMTQSPASQS ASLGESVTIT             180
CLASQTIGTW LAWYQQKPGK SPQFLIYAAT SLADGVPSRF SGSGSGTKFS FKISSLQAED             240
FVSYYCQQLY STPFTFGGGT KLEIK                                                   265

SEQ ID NO: 43               moltype = DNA   length = 795
FEATURE                     Location/Qualifiers
misc_feature                1..795
                            note = synthetic - 8D10
source                      1..795
                            mol_type = other DNA
                            organism = synthetic construct
SEQUENCE: 43
atggccttac cagtgaccgc cttgctcctg ccgctggcct tgctgctcca cgccgccagg              60
ccggatattg tgatgaccca gtctcctgcc tcccagtctg catctctggg agaaagtgtc             120
accatcacat gcctggcaag tcagaccatt ggtacatggt tagcatggta tcagcagaaa             180
ccagggaaat ctcctcagtt cctgatttat gctgcaacca gcttggcaga tggggtccca             240
tcaaggttca gtggtagtgg atctggcaca aaatttttct tcaagatcag cagcctacag             300
gctgaagatt ttgtaagtta ttactgtcaa caactttaca gtactccgtt cacgttcgga             360
gggggggacca agctggaaat aaaaggtggc ggtggctcgg gcggtggtgg gtcgggtggc            420
ggcggatctc aagtacagct gcaggagtct gggactgaac tggtgaagcc tggggcttca             480
gtgaagctgt cctgcaaggc ttctggctac accttcacca gctactggat gcactggatg             540
aagcagaggc ctggacaagg ccttgagtgg attggaaata ttaatcctag caatggtggt             600
actaactaca atgagaagtt caagaacaag gccacactga ctgtagacaa atcctccagc             660
acagcctaca tgcagctcag cagcctgaca tctgaggact ctgcggtcta ttattgtgca             720
agaagggatt attactacgg tagtagctac ggcttcgatg tctggggcac agggaccacg             780
gtcaccgtct cctca                                                              795

SEQ ID NO: 44               moltype = AA   length = 265
FEATURE                     Location/Qualifiers
REGION                      1..265
                            note = synthetic - 8D10
source                      1..265
```

```
                         mol_type = protein
                         organism = synthetic construct
SEQUENCE: 44
MALPVTALLL PLALLLHAAR PDIVMTQSPA SQSASLGESV TITCLASQTI GTWLAWYQQK   60
PGKSPQFLIY AATSLADGVP SRFSGSGSGT KFSFKISSLQ AEDFVSYYCQ QLYSTPFTFG  120
GGTKLEIKGG GGSGGGGSGG GGSQVQLQES GTELVKPGAS VKLSCKASGY TFTSYWMHWM  180
KQRPGQGLEW IGNINPSNGG TNYNEKFKNK ATLTVDKSSS TAYMQLSSLT SEDSAVYYCA  240
RRDYYYGSSY GFDVWGTGTT VTVSS                                      265

SEQ ID NO: 45           moltype = DNA  length = 780
FEATURE                 Location/Qualifiers
misc_feature            1..780
                        note = synthetic - 10C2
source                  1..780
                        mol_type = other DNA
                        organism = synthetic construct
SEQUENCE: 45
atggcctlac cagtgaccgc cttgctcctg ccgctggcct tgctgctcca cgccgccagg   60
ccgcaggtgc agctggagca gtctggacct gtgctggtga agcctggggc ttcagtgaag  120
atgtcctgta aggcttctgg atacacattc actgactact atatgaactg ggtgaagcag  180
agccatggaa agagccttga gtggattgga gttattaatc cttacaacgg tggtactagc  240
tacaaccaga agttcaaggg caaggccaca ttgactgttg acaagtcctc cagcacagcc  300
tgcatggagc tcaactgcct aacatctgag gactctgcag tctattactg taccctgggg  360
gcttactggg gtcaaggaac ctcagtcacc gtctcctcag gtggcggtgg ctcgggcggt  420
ggtgggtcgg gtggcggcgg atctgatatt gtgctgacac agactccact cactttgtcg  480
gttaccattg gacaaccagc ctccatctct gcaagtcaaa atcagagcct cttagatagt  540
tatggaaaga catatttgaa ttggttgtta cagaggccag gccagtctcc aaagcgccta  600
atctatctgg tgtctaaact ggactctgga gtccctgaca ggttcactgg cagtggatca  660
gggacagatt tcacactgaa aatcagcaga gtggaggctg aggatttggg agtttattat  720
tgctggcaag gtacacattt tcctcggacg ttcggtggag gcaccaagct ggaaatcaaa  780

SEQ ID NO: 46           moltype = AA  length = 260
FEATURE                 Location/Qualifiers
REGION                  1..260
                        note = synthetic - 10C2
source                  1..260
                        mol_type = protein
                        organism = synthetic construct
SEQUENCE: 46
MALPVTALLL PLALLLHAAR PQVQLEQSGP VLVKPGASVK MSCKASGYTF TDYYMNWVKQ   60
SHGKSLEWIG VINPYNGGTS YNQKFKGKAT LTVDKSSSTA CMELNCLTSE DSAVYYCTLG  120
AYWGQGTSVT VSSGGGGSGG GGSGGGGSDI VLTQTPLTLS VTIGQPASIS CKSNQSLLDS  180
YGKTYLNWLL QRPGQSPKRL IYLVSKLDSG VPDRFTGSGS GTDFTLKISR VEAEDLGVYY  240
CWQGTHFPRT FGGGTKLEIK                                            260

SEQ ID NO: 47           moltype = DNA  length = 790
FEATURE                 Location/Qualifiers
misc_feature            1..790
                        note = synthetic - 12B1
source                  1..790
                        mol_type = other DNA
                        organism = synthetic construct
SEQUENCE: 47
atggcctlac cagtgaccgc cttgctcctg ccgctggcct tgctgctcca cgccgccagg   60
ccggaggtca agctggagga gtcagggact gaactggtga agcctggggc ttcagtgaag  120
ctgtcctgca aggcttctgg ctacaccttc accagtactg gatgcactg ggtgaagcag   180
aggcctggac aaggccttga gtggattgga aatattaatc ctaccaatgg tgtactaac   240
tacaatgaga agttcaagag caaggccaca ctgactgtag acaaatcctc agaacagcc   300
tacatgcagc tcagcagcct gacatctggg gactcagcgg tctactattg tgcaagaagg  360
gactttatta ctacatccgg gtttgcttac tggggccaag ggactctggt cactgtctct  420
gcaggtggcg gtggctcggg cggtggtggg tcggtggcg gcggatctga tattgtgatg  480
acacagacta cagcctccct atctacatct gtgggagaaa ctgtcaccat cacatgtcga  540
gcaagtggga atcttcacag ttatttaaca tggtatcagc agaaacaggg aaagtctcct  600
cagctcctgg tctataatgc aaaaaccttg cagatggtg tgccatcaag gttcagtggc  660
agtggatcag gaacacaata ttctctcaag atcgacgcc tgcagcctga gattttgggg  720
agttattact gtcaacattt ttggactact ccattcacgt tcggctcggg gacaaagttg  780
gagataaaac                                                       790

SEQ ID NO: 48           moltype = AA  length = 263
FEATURE                 Location/Qualifiers
REGION                  1..263
                        note = synthetic - 12B1
source                  1..263
                        mol_type = protein
                        organism = synthetic construct
SEQUENCE: 48
MALPVTALLL PLALLLHAAR PEVKLEESGT ELVKPGASVK LSCKASGYTF TSYWMHWVKQ   60
RPGQGLEWIG NINPTNGGTN YNEKFKSKAT LTVDKSSRTA YMQLSSLTSG DSAVYYCARR  120
DFITTSGFAY WGQGTLVTVS AGGGGSGGGG SGGGGSDIVM TQTTASLSTS VGETVTITCR  180
```

```
ASGNLHSYLT WYQQKQGKSP QLLVYNAKTL ADGVPSRFSG SGSGTQYSLK IDSLQPEDFG   240
SYYCQHFWTT PFTFGSGTKL EIK                                          263

SEQ ID NO: 49           moltype = DNA  length = 799
FEATURE                 Location/Qualifiers
misc_feature            1..799
                        note = synthetic - 13H1
source                  1..799
                        mol_type = other DNA
                        organism = synthetic construct
SEQUENCE: 49
atggccttac cagtgaccgc cttgctcctg ccgctggcct tgctgctcca cgccgccagg    60
ccgcaagtcc agctgcagca gtctgggact gaactggtga agcctggggc ttcagtgaag   120
ctgtcctgca aggcttctgg ccacaccttc accagtactg gtgatgcact ggtgaagcag   180
aggcctggac aaggcttgag tggattggaa atattaatc ctagcaatgg tggtactaac   240
tacaatgaga agttcaagag caaggccaca ctgactgtag acaaatcctc cagcacagcc   300
tacatgcagc tcagcagcct gacatctgag gactctgcgg tctattattg tgcaagaagg   360
ggatactacg gtagtagcag ctactggtcc ttcgatgtct ggggcacagg gaccacggtc   420
accgtctcct caggtggcgg tggctcgggc ggtggtgggt cgggtggcgg cggatctgac   480
attgtgatga cccagactcc caaatccatg tccatgtcag taggagagag ggtcaccttg   540
agctgcaagg ccagtgagaa tgtgggtact tatgtatcct ggtatcaaca gaaaccagag   600
cagtctccta aagtgctgat atacggggca tccaaccggt tcactggggt ccccgatcgc   660
ttcacaggca gtggatctgc aacagatttc actctgacca tcagtagtgt gcagactgag   720
gaccttgcag attatcactg tggacagagt tacagctatc cgctcacgtt cggtgctggg   780
accaagctgg agctgaaac                                               799

SEQ ID NO: 50           moltype = AA  length = 266
FEATURE                 Location/Qualifiers
REGION                  1..266
                        note = synthetic - 13H1
source                  1..266
                        mol_type = protein
                        organism = synthetic construct
SEQUENCE: 50
MALPVTALLL PLALLLHAAR PQVQLQQSGT ELVKPGASVK LSCKASGHTF TSYWMHWVKQ    60
RPGQGLEWIG NINPSNGGTN YNEKFKSKAT LTVDKSSSTA YMQLSSLTSE DSAVYYCARR   120
GYYGSSSYWS FDVWGTGTTV TVSSGGGGSG GGGSGGGGSD IVMTQTPKSM SMSVGERVTL   180
SCKASENVGT YVSWYQQKPE QSPKVLIYGA SNRFTGVPDR FTGSGSATDF TLTISSVQTE   240
DLADYHCGQS YSYPLTFGAG TKLELK                                        266

SEQ ID NO: 51           moltype = DNA  length = 793
FEATURE                 Location/Qualifiers
misc_feature            1..793
                        note = synthetic - 15B8
source                  1..793
                        mol_type = other DNA
                        organism = synthetic construct
SEQUENCE: 51
atggccttac cagtgaccgc cttgctcctg ccgctggcct tgctgctcca cgccgccagg    60
ccgcaggttc agctggagca gtctgggact gaactggtga agcctggggc ttcagtgaag   120
ctgtcctgca aggcttctgg ctacaccttc accagtactg gtgatgcact ggtgaagcag   180
aggcctggac aaggcttgag tggattggaa atattaatc ctagcaatgg tggtactaac   240
tacaatgaga agttcaagag caaggccaca ctgactgtag acaaatcctc cagcacagcc   300
tacatgcagc tcagcagcct gacatctgag gactctgcga tctattattg tgcaagacgg   360
aataattact acgctagtag cccttttgct tactgggcc aagggactct ggtcagtgtc   420
tctgcaggtg gcggtggctc gggcggtggt gggtggcgcgg cggatc tgacattgtc   480
atgacacaga ctccagcctc cctatctgca tctgtgggag aaactgtcac catcacatgt   540
cgagcaagtg gaatattca caattattta gcatggtatc agcagaaaca gggaaaatct   600
cctcagctcc tggtctataa tgcaaaaacc ttagcagatg gtgtgccatc aaggttcagt   660
ggcagtggat caggaacaca atattctctc aagatcaaca gcctgcagcc tgaagatttt   720
gggagttatt actgtcaaca tttttggagt actccattca cgttcggctc ggggacaaag   780
ttggaaataa aac                                                     793

SEQ ID NO: 52           moltype = AA  length = 264
FEATURE                 Location/Qualifiers
REGION                  1..264
                        note = synthetic - 15B8
source                  1..264
                        mol_type = protein
                        organism = synthetic construct
SEQUENCE: 52
MALPVTALLL PLALLLHAAR PQVQLEQSGT ELVKPGASVK LSCKASGYTF TSYWMHWVKQ    60
RPGQGLEWIG NINPSNGGTN YNEKFKSKAT LTVDKSSSTA YMQLSSLTSE DSAIYYCARR   120
NNYYASSPFA YWGQGTLVSV SAGGGGSGGG GSGGGGSDIV MTQTPASLSA SVGETVTITC   180
RASGNIHNYL AWYQQKQGKS PQLLVYNAKT LADGVPSRFS GSGSGTQYSL KINSLQPEDF   240
GSYYCQHFWS TPFTFGSGTK LEIK                                          264

SEQ ID NO: 53           moltype = DNA  length = 1467
FEATURE                 Location/Qualifiers
```

```
misc_feature           1..1467
                       note = synthetic - 8D10 CAR
source                 1..1467
                       mol_type = other DNA
                       organism = synthetic construct
SEQUENCE: 53
atggccttac cagtgaccgc cttgctcctg ccgctggcct tgctgctcca cgccgccagg    60
ccgcaagtac agctgcagga gtctgggact gaactggtga agcctggggc ttcagtgaag   120
ctgtcctgca aggcttctgg ctacacctrc accagctact ggatgcactg gatgaagcac   180
aggcctggac aaggcttgga gtggattgga aatattaatc ctagcaatgg tggtactaac   240
tacaatgaga agttcaagaa caaggccaca ctgactgtag acaaatcctc cagcacagcc   300
tacatgcagc tcagcagcct gacatctgag gactctgcgg tctattattg tgcaagaagg   360
gattattact acggtagtag ctacggcttc gatgtctggg gcacagggac cacggtcacc   420
gtctcctcag gtggcggtgg ctcgggcggt ggtgggtcgg gtggcggcgg atctgatatt   480
gtgatgaccc agtctcctgc ctcccagtct gcatctctgg gagaaagtgt caccatcaca   540
tgcctggcaa gtcagaccat tggtacatgg ttagcatggt atcagcagaa accagggaaa   600
tctcctcagt tcctgattta tgctgcaacc agcttggcag atggggtccc atcaaggttc   660
agtggtagtg gatctggcac aaaatttcct ttcaagatca gcagcctaca ggctgaagat   720
tttgtaagtt attactgtca acaacttac agtactccgt tcacgttcgg aggggggacc   780
aagctggaaa taaaaccac gacgccagcg ccgcgaccac caacaccggc gcccaccatc   840
gcgtcgcagc ccctgtccct gcgcccagag gcgtgccggc cagcggcggg gggcgcagtg   900
cacacgaggg ggctggactt cgcctgtgat atctacatct gggcgccctt ggccgggact   960
tgtggggtcc ttctcctgtc actggttatc acccttact gcaaacgggg cagaaagaaa  1020
ctcctgtata tattcaaaca accatttatg agaccagtac aaactactca agaggaagat  1080
ggctgtagct gccgatttcc agaagaagaa gaaggaggat gtgaactgag agtgaagttc  1140
agcaggagcg cagacgcccc cgcgtacaag cagggccaga accagctcta taacgagctc  1200
aatctaggac gaagagagga gtacgatgtt ttggacaaga cgtggccg ggaccctgag  1260
atgggggaa agccgagaag gaagaaccct caggaaggcc tgtacaatga actgcagaaa  1320
gataagatgg cggaggccta cagtgagatt gggatgaaag cgagcgccg gaggggcaag  1380
gggcacgatg gcctttacca gggtctcagt acagccacca aggacaccta cgacgccttt  1440
cacatgcagg ccctgccccc tcgctag                                     1467

SEQ ID NO: 54           moltype = AA length = 488
FEATURE                 Location/Qualifiers
REGION                  1..488
                        note = synthetic - 8D10 CAR
source                  1..488
                        mol_type = protein
                        organism = synthetic construct
SEQUENCE: 54
MALPVTALLL PLALLLHAAR PQVQLQESGT ELVKPGASVK LSCKASGYTF TSYWMHWMKQ    60
RPGQGLEWIG NINPSNGGTN YNEKFKNKAT LTVDKSSSTA YMQLSSLTSE DSAVYYCARR   120
DYYYGSSYGF DVWGTGTTVT VSSGGGGSGG GGSGGGGSDI VMTQSPASQS ASLGESVTIT   180
CLASQTIGTW LAWYQQKPGK SPQFLIYAAT SLADGVPSRF SGSGSGTKFS FKISSLQAED   240
FVSYYCQQLY STPFTFGGGT KLEIKTTTPA PRPPTPAPTI ASQPLSLRPE ACRPAAGGAV   300
HTRGLDFACD IYIWAPLAGT CGVLLLSLVI TLYCKRGRKK LLYIFKQPFM RPVQTTQEED   360
GCSCRFPEEE EGGCELRVKF SRSADAPAYK QGQNQLYNEL NLGRREEYDV LDKRRGRDPE   420
MGGKPRRKNP QEGLYNELQK DKMAEAYSEI GMKGERRRGK GHDGLYQGLS TATKDTYDAL   480
HMQALPPR                                                           488

SEQ ID NO: 55           moltype = DNA length = 672
FEATURE                 Location/Qualifiers
misc_feature            1..672
                        note = synthetic
source                  1..672
                        mol_type = other DNA
                        organism = synthetic construct
SEQUENCE: 55
accacgacgc cagcgccgcg accaccaaca ccggcgccca ccatcgcgtc gcagcccctg    60
tccctgcgcc cagaggcgtg ccggccagcg gcggggggcg cagtgcacac gagggggctg   120
gacttcgcct gtgatatcta catctgggcg cccttggccg ggacttgtgg ggtccttctc   180
ctgtcactgg ttatcaccct ttactgcaaa cggggcagaa agaaactcct gtatatattc   240
aaacaaccat ttatgagacc agtacaaact actcaagagg aagatggctg tagctgccga   300
tttccagaag aagaaggaggat gtgaactgag agtcagcag gagcgcagac gcccccgcgt   360
acaagcaggg ccagaaccag ctctataacg agctcaatct aggacgaaga   420
gaggagtacg atgttttgga caagacgtgg ccgggaccct gagatgggg gaaagccg    480
agaaggaaga accctcagga aggcctgtac aatgaactgc agaaagataa gatggcggag   540
gcctacagtg agattggat gaaagcgag cgccggaggg caaggggca cgatggcctt   600
taccagggtc tcagtacagc caccaaggac acctacgacg cccttcacat gcaggccctg   660
ccccctcgct ag                                                     672

SEQ ID NO: 56           moltype = AA length = 223
FEATURE                 Location/Qualifiers
REGION                  1..223
                        note = synthetic
source                  1..223
                        mol_type = protein
                        organism = synthetic construct
SEQUENCE: 56
```

-continued

```
TTTPAPRPPT PAPTIASQPL SLRPEACRPA AGGAVHTRGL DFACDIYIWA PLAGTCGVLL  60
LSLVITLYCK RGRKKLLYIF KQPFMRPVQT TQEEDGCSCR FPEEEEGGCE LRVKFSRSAD 120
APAYKQGQNQ LYNELNLGRR EEYDVLDKRR GRDPEMGGKP RRKNPQEGLY NELQKDKMAE 180
AYSEIGMKGE RRRGKGHDGL YQGLSTATKD TYDALHMQAL PPR                  223
```

ANTI-CD30 ANTIBODIES

CROSS-REFERENCE TO RELATED APPLICATIONS

This application is a continuation of U.S. patent application Ser. No. 16/580,483, filed Sep. 24, 2019, which claims priority to U.S. Provisional Application No. 62/735,508, filed on Sep. 24, 2018, the contents of each of which are incorporated by reference in their entirety.

STATEMENT REGARDING FEDERALLY SPONSORED RESEARCH

N/A

SEQUENCE LISTING

A Sequence Listing accompanies this application and is submitted as an XML file of the sequence listing named "650053_00937.xml" which is 79,729 bytes in size and was created on Feb. 1, 2023. The sequence listing is electronically submitted via Patent Center with the application and is incorporated herein by reference in its entirety.

BACKGROUND OF THE INVENTION

The field of the invention is novel antibodies specific to human CD30, and the use thereof.

CD30 cell surface molecule is a member of the tumor necrosis factor receptor (TNF-R) superfamily and a transmembrane glycoprotein preferentially expressed by activated lymphoid cells. This family of molecules has variable homology among its members and includes nerve growth factor receptor (NGFR), CD120 (a), CD120 (b), CD27, CD40 and CD95. Members of this family play a role in regulating proliferation and differentiation of lymphocytes.

CD30 was originally identified by the monoclonal antibody Ki-1, which is reactive with antigens expressed on Hodgkin and Reed-Sternberg cells of Hodgkin's disease (Schwab et al., Nature 299:65 (1982)). CD30 has been used as a clinical marker for Hodgkin's lymphoma and related hematological malignancies (Froese et al., J. Immunol. 139: 2081 (1987); Carde et al., Eur. J. Cancer 26:474 (1990)). It has since been found on a number of hematologic malignancies. Since the percentage of CD30-positive cells in normal individuals is very low, CD30 in tumor cells renders it an important target for antibody mediated therapy to specifically target therapeutic agents against CD30-positive neoplastic cells (Chaiarle, R., et al. Clin. Immunol. 90 (2): 157-164 (1999)).

Hodgkin Lymphoma (HL) is often treatable, with 86% surviving over 5 years. However, about 30% of patients relapse, a subset of which develop resistant HL. Refractory or relapsed chemo-resistant disease is more challenging to treat: the 5-year survival rate for these patients is just 31%. CD30 is also expressed in a substantial subset of patients with acute myeloid leukemia (AML), which accounts for 1.2% of all cancer cases in the United States and has a 5-year survival rate of just 26.6%. Relapse following initial therapy is common, and patients who relapse after a stem cell transplantation are typically non-responsive to further therapeutic intervention.

Accordingly, the need exists for improved therapeutic antibodies against CD30 which are effective at treating and/or preventing diseases mediated by CD30 including HL and AML.

SUMMARY OF THE INVENTION

The present invention addresses the aforementioned need by providing isolated specific CD30 antibodies and antigen binding fragments thereof. The antibodies described herein can be used for methods of detecting, treating, and stratifying patient populations as detailed more below.

In one aspect, the present disclosure provides an isolated antibody or antigen binding fragment thereof capable of binding human CD30 comprising:
(a) a light chain variable domain comprising a CDRL1 region of SEQ ID NO:2, a CDRL2 region of SEQ ID NO:3, and a CDRL3 region of SEQ ID NO:4 and a heavy chain variable domain comprising a CDRH1 region of SEQ ID NO:6, a CDRH2 region of SEQ ID NO: 7, and a CDRH3 region of SEQ ID NO:8;
(b) a light chain variable domain comprising a CDRL1 region of SEQ ID NO: 10, a CDRL2 region of SEQ ID NO:11, and a CDRL3 region of SEQ ID NO:12 and a heavy chain variable domain comprising a CDRH1 region of SEQ ID NO:14, a CDRH2 region of SEQ ID NO:15, and a CDRH3 region of GAY,
(c) a light chain variable domain comprising a CDRL1 region of SEQ ID NO: 18, a CDRL2 region of SEQ ID NO:19, and a CDRL3 region of SEQ ID NO:20 and a heavy chain variable domain comprising a CDRH1 region of SEQ ID NO:22, a CDRH2 region of SEQ ID NO:23, and a CDRH3 region of SEQ ID NO:24,
(d) a light chain variable domain comprising a CDRL1 region of SEQ ID NO: 26, a CDRL2 region of SEQ ID NO:27, and a CDRL3 region of SEQ ID NO:28 and a heavy chain variable domain comprising a CDRH1 region of SEQ ID NO:30, a CDRH2 region of SEQ ID NO:31, and a CDRH3 region of SEQ ID NO:32, or
(e) a light chain variable domain comprising a CDRL1 region of SEQ ID NO: 34, a CDRL2 region of SEQ ID NO:35, and a CDRL3 region of SEQ ID NO:36 and a heavy chain variable domain comprising a CDRH1 region of SEQ ID NO:38, a CDRH2 region of SEQ ID NO:39, and a CDRH3 region of SEQ ID NO:40.

In another aspect, the present disclosure provides isolated antibody or antigen fragment thereof comprising a heavy and a light chain selected from the group consisting of: (a) a light chain comprising SEQ ID NO:1 or a sequence with at least 85% similarity to SEQ ID NO: 1, and a heavy chain comprising SEQ ID NO:5 or a sequence with at least 85% similarity to SEQ ID NO:5; (b) a light chain comprising SEQ ID NO:9 or a sequence with at least 85% similarity to SEQ ID NO:9, and a heavy chain comprising SEQ ID NO:13 or a sequence with at least 85% similarity to SEQ ID NO:13; (c) a light chain comprising SEQ ID NO: 17 or a sequence with at least 85% similarity to SEQ ID NO:17, and a heavy chain comprising SEQ ID NO:21 or a sequence with at least 85% similarity to SEQ ID NO:21; (d) a light chain comprising SEQ ID NO:25 or a sequence with at least 85% similarity to SEQ ID NO: 25, and a heavy chain comprising SEQ ID NO:29 or a sequence with at least 85% similarity to SEQ ID NO:29; and (e) a light chain comprising SEQ ID NO:33 or a sequence with at least 85% similarity to SEQ ID NO:33, and a heavy chain comprising SEQ ID NO:37 or a sequence with at least 85% similarity to SEQ ID NO:37.

In another aspect, the disclosure provides an isolated nucleic acid molecule which encodes the antibody or antigen binding fragment thereof described herein.

In yet another aspect, the disclosure provides an expression vector comprising the nucleic acid molecule encoding the antibody or antigen binding fragment thereof specific to CD30 described herein.

In another aspect, the disclosure provides a composition comprising a CD30 specific antibody or antigen binding fragment thereof and a carrier.

In another aspect, the disclosure provides a method of treating a patient having a CD30$^+$ cancer, the method comprising administering a therapeutically effective amount of the isolated antibody or antigen binding fragment thereof capable of binding human CD30 in order to treat the cancer.

In yet a further aspect, the disclosure provides a method of inhibiting growth of a tumor cell expressing CD30 comprising contacting the tumor cell with an effective amount of the antibody or antigen binding fragment thereof specific for CD30 such that the growth of the cell is inhibited.

In another aspect, the disclosure provides chimeric antigen receptor (CAR) comprising a CD30 binding domain or scFvs described herein. In one aspect, the disclosure provides chimeric antigen receptor (CAR) comprising a CD30 binding domain (a) a light chain variable domain comprising a CDRL1 region of SEQ ID NO:2, a CDRL2 region of SEQ ID NO: 3, and a CDRL3 region of SEQ ID NO:4 and a heavy chain variable domain comprising a CDRH1 region of SEQ ID NO:6, a CDRH2 region of SEQ ID NO:7, and a CDRH3 region of SEQ ID NO:8; (b) a light chain variable domain comprising a CDRL1 region of SEQ ID NO: 10, a CDRL2 region of SEQ ID NO:11, and a CDRL3 region of SEQ ID NO:12 and a heavy chain variable domain comprising a CDRH1 region of SEQ ID NO:14, a CDRH2 region of SEQ ID NO:15, and a CDRH3 region of GAY, (c) a light chain variable domain comprising a CDRL1 region of SEQ ID NO:18, a CDRL2 region of SEQ ID NO:19, and a CDRL3 region of SEQ ID NO:20 and a heavy chain variable domain comprising a CDRH1 region of SEQ ID NO: 22, a CDRH2 region of SEQ ID NO:23, and a CDRH3 region of SEQ ID NO:24, (d) a light chain variable domain comprising a CDRL1 region of SEQ ID NO:26, a CDRL2 region of SEQ ID NO:27, and a CDRL3 region of SEQ ID NO:28 and a heavy chain variable domain comprising a CDRH1 region of SEQ ID NO:30, a CDRH2 region of SEQ ID NO:31, and a CDRH3 region of SEQ ID NO:32, or (e) a light chain variable domain comprising a CDRL1 region of SEQ ID NO:34, a CDRL2 region of SEQ ID NO:35, and a CDRL3 region of SEQ ID NO: 36 and a heavy chain variable domain comprising a CDRH1 region of SEQ ID NO:38, a CDRH2 region of SEQ ID NO:39, and a CDRH3 region of SEQ ID NO:40.

In another aspect, the disclosure provides CAR comprising an CD30 binding domain comprises a heavy and a light chain selected from the group consisting of: (a) a light chain comprising SEQ ID NO:1 or a sequence with at least 85% similarity to SEQ ID NO:1, and a heavy chain comprising SEQ ID NO:5 or a sequence with at least 85% similarity to SEQ ID NO: 5; (b) a light chain comprising SEQ ID NO:9 or a sequence with at least 85% similarity to SEQ ID NO:9, and a heavy chain comprising SEQ ID NO:13 or a sequence with at least 85% similarity to SEQ ID NO:13; (c) a light chain comprising SEQ ID NO:17 or a sequence with at least 85% similarity to SEQ ID NO:17, and a heavy chain comprising SEQ ID NO:21 or a sequence with at least 85% similarity to SEQ ID NO:21; (d) a light chain comprising SEQ ID NO: 25 or a sequence with at least 85% similarity to SEQ ID NO:25, and a heavy chain comprising SEQ ID NO:29 or a sequence with at least 85% similarity to SEQ ID NO:29; and (e) a light chain comprising SEQ ID NO:33 or a sequence with at least 85% similarity to SEQ ID NO: 33, and a heavy chain comprising SEQ ID NO:37 or a sequence with at least 85% similarity to SEQ ID NO:37.

In another aspect, the disclosure provides an effector cell expressing the CAR described herein.

The foregoing and other aspects and advantages of the invention will appear from the following description. In the description, reference is made to the accompanying drawings which form a part hereof, and in which there are shown, by way of illustration, preferred embodiments of the invention. Such embodiments do not necessarily represent the full scope of the invention, however, and reference is made therefore to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A depicts the percent identity between the light chains of the novel CD30 antibodies to each other and the known CD30 antibody AC10.

FIG. 3B depicts the percent identity between the heavy chains of the novel CD30 antibodies to each other and the known CD30 antibody AC10.

FIGS. 16A-16D depicts the sequences of some examples of the CD30 scFv and CARs and components thereof of the present invention.

DETAILED DESCRIPTION OF THE INVENTION

The present invention provides isolated antibodies, e.g., monoclonal antibodies, single chain antibodies and antigen-binding fragments thereof, which specifically/selectively bind to human CD30 and other therapeutic compositions containing such antibodies, alone or in combination with additional therapeutic agents. Also provided are methods for detecting CD30 expression and methods of treating CD30 mediated diseases using the antibodies and compositions thereof.

Figures 14, 15:
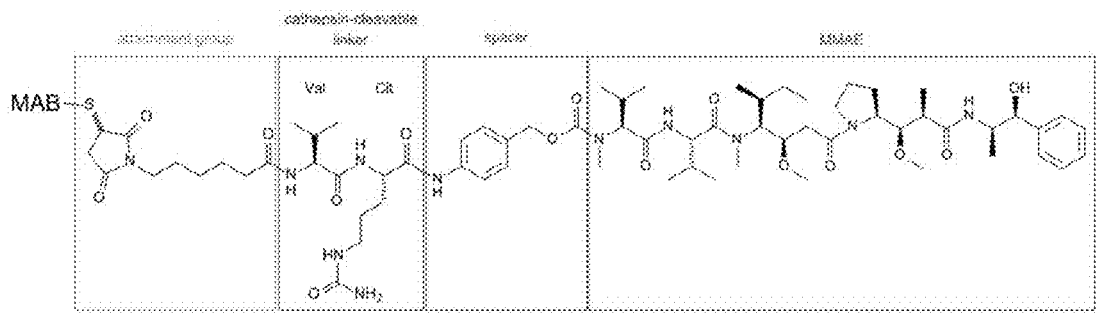
FIG. 14 is an exemplary conjugate of the monoclonal antibody (MAB) of the present invention.
FIG. 15 demonstrates surface plasmon resonance (SPR) analysis of CD30 mAbs using two approaches. (A) CD30 protein was immobilized on a CM5 chip, and the antibodies were flowed as an analyte to assess affinity. (B) 8D10, 10C2, or AC10 antibody was immobilized on a Protein G chip, and CD30 protein was flowed as an analyte to assess affinity.

The present disclosure provides in one embodiment an isolated antibody or antigen-binding fragment thereof capable of selectively binding to human CD30, and having a different binding specificity to CD30 (i.e., they bind to a different epitope) than the known anti-CD30 antibody AC10 (monoclonal antibody in brentuximab). By "selectively" or "specifically" we mean an antibody capable of binding human CD30 but does not bind to other CD molecules or other cell surface proteins. By binding, we mean that the antibodies are capable of detecting CD30 protein at a given tissue's extracellular membrane by standard methods (e.g., tissue section immunofluorescence assays or flow cytometry). In the Examples of the present invention, binding was characterized by surface plasmon resonance, as shown in FIG. 15.

The term "$K_d$", as used herein, is intended to refer to the dissociation constant of a particular antibody-antigen interaction.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, NJ). For further descriptions, see Jönsson, U., et al. (1993) Ann. Biol. Clin. 51:19-26; Jönsson, U., et al. (1991) Biotechniques 11:620-627; Johnsson, B., et al. (1995) J. Mol. Recognit. 8:125-131; and Johnson, B., et al. (1991) Anal. Biochem. 198:268-277.

The terms "antibody" or "antibody molecule" are used herein interchangeably and refer to immunoglobulin molecules or other molecules which comprise an antigen binding domain. The term "antibody" or "antibody molecule" as used herein is thus intended to include whole antibodies (e.g., IgG, IgA, IgE, IgM, or IgD), monoclonal antibodies, chimeric antibodies, humanized antibodies, and antibody fragments, including single chain variable fragments (ScFv), single domain antibody, and antigen-binding fragments, genetically engineered antibodies, among others, as long as the characteristic properties (e.g., ability to bind CD30) are retained. By "antibody" we mean to include monoclonal antibodies, e.g., 8D10, 10C2, 12B1, 13H1, 15B8, made from hybridoma cell lines, antigen binding fragments thereof, including antibody fragments or peptides that contain the antigen-binding domain (e.g., CDR domains within the newly isolated monoclonal antibodies), single chain antibodies and humanized versions of the antibodies described.

As stated above, the term "antibody" includes "antibody fragments" or "antibody-derived fragments" and "antigen binding fragments" which comprise an antigen binding domain. The term "antibody fragment" as used herein is intended to include any appropriate antibody fragment that displays antigen binding function, for example, Fab, Fab', F(ab')2, scFv, Fv, dsFv, ds-scFv, Fd, dAbs, TandAbs dimers, mini bodies, monobodies, diabodies, and multimers thereof and bispecific antibody fragments. Antibodies can be genetically engineered from the CDRs and monoclonal antibody sequences described herein into antibodies and antibody fragments by using conventional techniques such as, for example, synthesis by recombinant techniques or chemical synthesis. Techniques for producing antibody fragments are well known and described in the art.

One may wish to engraft one or more CDRs from the monoclonal antibodies described herein into alternate scaffolds. For example, standard molecular biological techniques can be used to transfer the DNA sequences encoding the antibody's CDR(s) to (1) full IgG scaffold of human or other species; (2) a scFv scaffold of human or other species, or (3) other specialty vectors. If the CDR(s) have been transferred to a new scaffold all of the previous modifications described can also be performed. For example, one could consult *Biotechnol Genet Eng Rev*, 2013, 29:175-86 for a review of useful methods.

Figure 1:
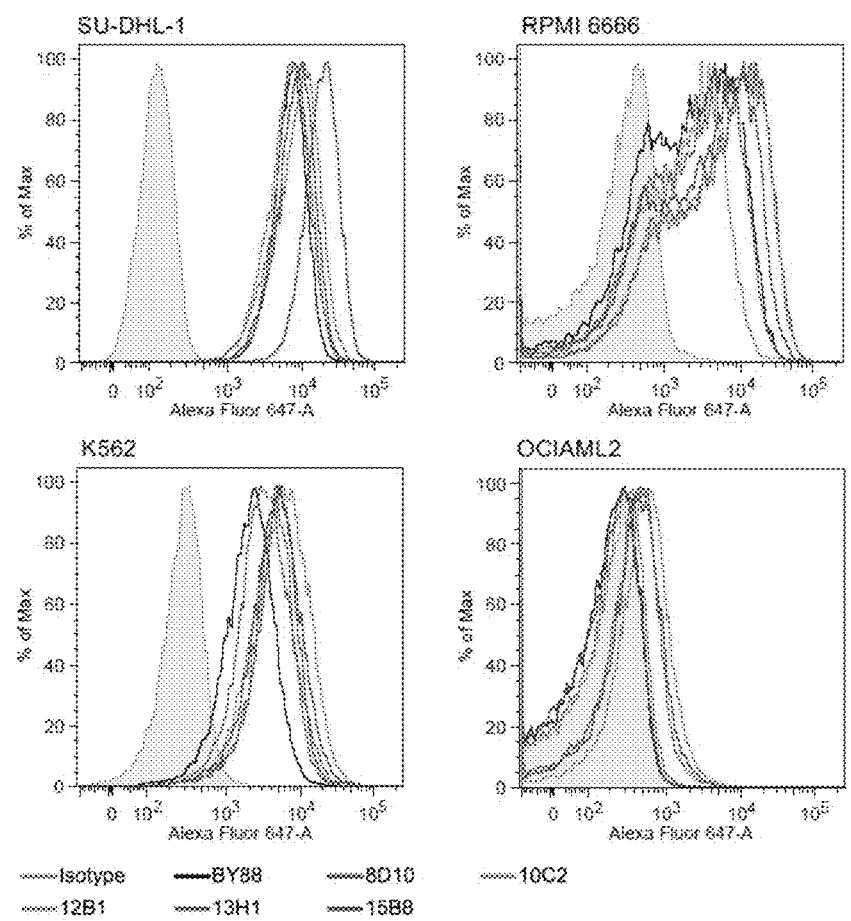
FIG. 1 depict the specific binding of novel CD30 antibody clones to CD30– and CD30+ cells. Flow cytometry analysis was preformed using purified antibody on CD30+ cell lines (SU-DHL-1, RPMI6666, 562) and a CD30-cell line (OCIAML2). A commercially available α-huCD30 antibody (clone BY88) and an isotype control were also tested.

The present invention provides, in one embodiment, monoclonal antibodies (MAbs) that target CD30 and derivatives thereof. Suitable monoclonal antibodies include, but are not limited to, monoclonal antibodies 8D10, 10C2, 12B1, 13H1, and 15B8 produced from hybridoma cell lines as described in the Examples disclosed herein. Specific binding of the mAbs to cell-surface expressed CD30 was assessed by flow cytometry (FIG. 1). Each of five hybridoma clones, designated as 8D10, 10C2, 12B1, 13H1, and 15B8, bound to CD30+ but not CD30-cell lines indicating specificity for the selected antigen CD30.

In one embodiment, the present disclosure provides an isolated antibody or antigen binding fragment thereof capable of binding human CD30 comprising, consisting or consisting essentially of: (a) a light chain variable domain comprising a CDRL1 region of SEQ ID NO: 2, a CDRL2 region of SEQ ID NO:3, and a CDRL3 region of SEQ ID NO:4 and a heavy chain variable domain comprising a CDRH1 region of SEQ ID NO:6, a CDRH2 region of SEQ ID NO:7, and a CDRH3 region of SEQ ID NO:8; (b) a light chain variable domain comprising a CDRL1 region of SEQ ID NO:10, a CDRL2 region of SEQ ID NO:11, and a CDRL3 region of SEQ ID NO:12 and a heavy chain variable domain comprising a CDRH1 region of SEQ ID NO:14, a CDRH2 region of SEQ ID NO:15, and a CDRH3 region of GAY, (c) a light chain variable domain comprising a CDRL1 region of SEQ ID NO:18, a CDRL2 region of SEQ ID NO:19, and a CDRL3 region of SEQ ID NO:20 and a heavy chain variable domain comprising a CDRH1 region of SEQ ID NO:22, a CDRH2 region of SEQ ID NO:23, and a CDRH3 region of SEQ ID NO:24, (d) a light chain variable domain comprising a CDRL1 region of SEQ ID NO:26, a CDRL2 region of SEQ ID NO:27, and a CDRL3 region of SEQ ID NO: 28 and a heavy chain variable domain comprising a CDRH1 region of SEQ ID NO:30, a CDRH2 region of SEQ ID NO:31, and a CDRH3 region of SEQ ID NO:32, or (e) a light chain variable domain comprising a CDRL1 region of SEQ ID NO:34, a CDRL2 region of SEQ ID NO:35, and a CDRL3 region of SEQ ID NO:36 and a heavy chain variable domain comprising a CDRH1 region of SEQ ID NO:38, a CDRH2 region of SEQ ID NO:39, and a CDRH3 region of SEQ ID NO:40.

In one embodiment, the isolated antibody or antigen-binding fragment thereof comprises, consists essentially of or consists of a heavy and a light chain, wherein the antigen binding domain formed by the heavy and light chain is able to bind specifically to human CD30. In another embodiment, the antigen-binding fragment thereof comprises one or more CDRs from the heavy chain as described herein as the heavy chain in some instances contains the necessary requirement for antigen binding.

In one embodiment, the isolated antibody or antigen-binding fragment thereof comprises, consists essentially of or consists of a light chain comprising SEQ ID NO:1 or a sequence with at least 85% similarity to SEQ ID NO:1, and a heavy chain comprising SEQ ID NO: 5 or a sequence with at least 85% similarity to SEQ ID NO:5.

In another embodiment, the isolated antibody or antigen-binding fragment thereof comprises, consists essentially of or consists of a light chain comprising SEQ ID NO:9 or a sequence with at least 85% similarity to SEQ ID NO:9, and a heavy chain comprising SEQ ID NO: 13 or a sequence with at least 85% similarity to SEQ ID NO:13.

In another embodiment, the isolated antibody or antigen-binding fragment thereof comprises, consists essentially of or consists of a light chain comprising SEQ ID NO:17 or a sequence with at least 85% similarity to SEQ ID NO:17, and a heavy chain comprising SEQ ID NO:21 or a sequence with at least 85% similarity to SEQ ID NO:21.

In another embodiment, the isolated antibody or antigen-binding fragment thereof comprises, consists essentially of or consists of a light chain comprising SEQ ID NO:25 or a sequence with at least 85% similarity to SEQ ID NO:25, and a heavy chain comprising SEQ ID NO:29 or a sequence with at least 85% similarity to SEQ ID NO:29; and In another embodiment, the isolated antibody or antigen-binding fragment thereof comprises, consists essentially of or consists of a light chain comprising SEQ ID NO:33 or a sequence with at least 85% similarity to SEQ ID NO:33, and a heavy chain comprising SEQ ID NO:37 or a sequence with at least 85% similarity to SEQ ID NO:37.

In one embodiment, the monoclonal antibody is 8D10. In another embodiment, the monoclonal antibody is 10C2. In another embodiment, the monoclonal antibody is 12B1. In another embodiment, the monoclonal antibody is 13H1. In another embodiment, the monoclonal antibody is 15B8.

In some embodiments, the isolated antibody or antigen-binding fragment thereof is selected from the group consisting of a monoclonal antibody, a humanized antibody, a single chain variable fragment (scFv) antibody, a single domain antibody, an antigen-binding fragment and a chimeric antibody.

In one embodiment, the isolated antibody is a monoclonal antibody. In one embodiment, the monoclonal antibody is a mouse antibody. In another embodiment, the monoclonal antibody is a recombinant antibody or chimeric antibody. In a further embodiment, the monoclonal antibody is a humanized antibody.

In another embodiment, the antibody is an IgG antibody, for example, an IgG antibody selected from IgG1, IgG2a, IgG2b, IgG3, and IgG4.

In another embodiment, the isolated antibody or antigen fragment thereof described herein is engrafted within a full IgG scaffold or a scFv scaffold. As used herein, the term "scaffold" refers to the regions of an antibody that lie outside of the antigen binding domain, including in some examples the constant regions of the antibody. In one embodiment, the scaffold is a mammalian scaffold. In another embodiment, the scaffold is a human scaffold. For example, in one embodiment, human chimeric or humanized antibodies are derived in the present invention. Suitable methods and scaffolds are known in the art. For example, methods of CDR grafting are known in the art.

The terms "monoclonal antibody" or "monoclonal antibody composition" as used herein refer to a preparation of antibody molecules of a single amino acid composition that specifically binds to a single epitope of the antigen.

The term "chimeric antibody" refers to an antibody comprising a variable region, i.e., binding region, from one source or species and at least a portion of a constant region derived from a different source or species, usually prepared by recombinant DNA techniques. Other forms of "chimeric antibodies" are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art.

The term "antibody" shall include humanized antibody, chimeric antibody and recombinant human antibody. The monoclonal antibody also includes "humanized monoclonal antibody" and "human antibodies" which refers to antibodies displaying a single binding specificity for the antigen of interest (e.g., CD30) that have constant regions derived from human germline immunoglobulin sequences. In other words, the term "humanized antibody" refers to antibodies in which the human framework have been modified to comprise fragments of antibodies taken from a different species that provide specificity to an antigen (e.g., CD30) but in all other ways are human antibodies. The human monoclonal antibodies can be produced by a expressing the humanized antibody in a host cell (e.g., cell line).

The antibodies disclosed in the present invention may be modified to be humanized antibodies which include the constant region from a human germline immunoglobulin sequences. The term "recombinant human antibody" or "humanized antibody" includes all human antibodies that are prepared, expressed, created or isolated by recombinant means, such as antibodies isolated from a host cell such as an SP2-0, NS0 or CHO cell (like CHO K1) or from an animal (e.g., a mouse) that is transgenic for human immunoglobulin genes, antibodies, or polypeptides expressed using a recombinant expression vector transfected into a host cell. Such recombinant human antibodies have variable and in some embodiments, constant regions derived from human germline immunoglobulin sequences in a rearranged form.

For example, a humanized antibody may comprise the constant regions derived from the human germline immunoglobulin sequence and the "framework" (FR) variable domain residues which are the variable domain residues other than the hypervariable regions (CDRs). The framework of the variable domain usually consists of four FR domains (between the three CDRs, e.g., FR1, FR2, FR3 and FR4) for both the heavy and light chain (e.g., for light chain region would contain: FRL1-CDRL1-FRL2-CDRL2-FRL3-CDRL3-FRL4). Therefore, a humanized antibody may have the scaffold (e.g., constant regions and framework from a human immunoglobulin) and the CDRs or hypervariable regions from the mouse monoclonal antibodies described herein.

The term "fragment" as used herein refers to fragments of biological relevance (functional fragment), e.g., fragments which can contribute to or enable antigen binding, e.g., form part or all of the antigen binding site or can contribute to the prevention of the antigen interacting with its natural ligands. Fragments in some embodiments comprise a heavy chain variable region ($V_H$ domain) and light chain variable region ($V_L$) of the invention. In some embodiments, the fragments comprise one or more of the heavy chain complementarity determining regions (CDRHs) of the antibodies or of the $V_H$ domains, and one or more of the light chain complementarity determining regions (CDRLs), or $V_L$ domains to form the antigen binding site. For example, a fragment is suitable for use in the present methods and kits if it retains its ability to bind CD30. In some instances, "antigen-binding fragments" of an antibody include, for Example, (i) a Fab fragment, a monovalent fragment consisting of the VL, VH, CL and CH1 domains; (ii) a F(ab') 2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR).

The term "complementarity determining regions" or "CDRs," as used herein, refers to part of the variable chains of immunoglobulins (antibodies) and T cell receptors, generated by B-cells and T-cells respectively, through which these molecules bind to their specific antigen. As the most variable parts of the molecules, CDRs are crucial to the diversity of antigen specificities generated by lymphocytes. There are three CDRs (CDR1, CDR2 and CDR3), arranged non-consecutively, on the amino acid sequence of a variable domain of an antigen binding site. Since the antigen binding sites are typically composed of two variable domains (on two different polypeptide chains, heavy and light chain), there are six CDRs for each antigen binding site. Thus, six CDRs may collectively come into contact with the antigen. A single whole antibody molecule has two antigen binding sites and therefore contains twelve CDRs. Sixty CDRs can be found on a pentameric IgM molecule.

Within the variable domain, CDR1 and CDR2 may be found in the variable (V) region of a polypeptide chain, and CDR3 includes some of V, all of diversity (D, heavy chains only) and joining (J) regions. Since most sequence variation associated with immunoglobulins and T cell receptors is found in the CDRs, these regions are sometimes referred to as hypervariable regions. Among these, CDR3 shows the greatest variability as it is encoded by a recombination of VJ in the case of a light chain region and VDJ in the case of heavy chain regions. The tertiary structure of an antibody is important to analyze and design new antibodies.

As used herein, the terms "proteins" and "polypeptides" are used interchangeably herein to designate a series of amino acid residues connected to the other by peptide bonds between the alpha-amino and carboxy groups of adjacent residues. The terms "protein" and "polypeptide" refer to a polymer of protein amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to an encoded gene product and fragments thereof. Thus, exemplary polypeptides or proteins include gene products, naturally occurring proteins, homologs, orthologs, paralogs, fragments and other equivalents, variants, fragments, and analogs of the foregoing. The antibodies of the present invention are polypeptides, as well the antigen-binding fragments and fragments thereof.

In some embodiments, the antibodies comprise a light and a heavy chain that have substantial identity to the polypeptide sequences found in SEQ ID NOs: 1 and 5, 9 and 13, 17 and 21, 25 and 29, 33 and 37 respectively, or substantial identity in the CDR regions within the heavy and light chain of the antibody or antigen-binding fragment thereof as described herein.

In some embodiments, the antibodies have at least 85% identity to the light chain and heavy chain found in SEQ ID NOs: 1 and 5, 9 and 13, 17 and 21, 25 and 29, 33 and 37 respectively, alternatively at least 90% sequence identity to the light chain and heavy chain found in SEQ ID NOs: 1 and 5, 9 and 13, 17 and 21, 25 and 29, 33 and 37 respectively, alternatively at least 95% sequence identity to the light chain and heavy chain found in SEQ ID NOs: 1 and 5, 9 and 13, 17 and 21, 25 and 29, 33 and 37 respectively, alternatively at least 97% sequence identity to the light chain and heavy chain found in SEQ ID NOs: 1 and 5, 9 and 13, 17 and 21, 25 and 29, 33 and 37 respectively, alternatively at least 98% sequence identity to the light chain and heavy chain found in SEQ ID NOs: 1 and 5, 9 and 13, 17 and 21, 25 and 29, 33 and 37 respectively, alternatively at least 100% sequence identity to the light chain and heavy chain found in SEQ ID NOs: 1 and 5, 9 and 13, 17 and 21, 25 and 29, 33 and 37 respectively.

In some embodiments, the antibodies have at least 85% identity to the CDR domains described herein, alternatively at least 90% sequence identity, alternatively at least 95% sequence identity, alternatively at least 97% sequence identity, alternatively at least 98% sequence identity, alternatively at least 100% sequence identity. In some embodiments, the antibody or antigen binding fragment thereof has at least 85-100% sequence identity within CDRH1, CDRH2 and CDRH3 within SEQ ID NO:5 (e.g., SEQ ID Nos. 6-8), SEQ ID NO:13 (e.g., SEQ ID Nos: 14-16), SEQ ID NO:21 (e.g., SEQ ID Nos: 22-24), SEQ ID NO:29 (e.g., SEQ ID Nos: 30-32), or SEQ ID NO:37 (e.g., SEQ ID NOS: 38-40) and/or at least 85%-100% sequence identity within CDRL1, CDRL2 and CDRL3 within SEQ ID NO:1 (e.g. SEQ ID Nos. 2-4), SEQ ID NO:9 (e.g., SEQ ID Nos: 10-12), SEQ ID NO:17 (e.g., SEQ ID NOs. 18-20), SEQ ID NO:25 (e.g., SEQ ID Nos: 26-28), or SEQ ID NO:33 (e.g., SEQ ID Nos: 34-36).

In one embodiment, the antibody or antigen binding fragment thereof has at least 95-100% sequence identity within CDRH1, CDRH2 and CDRH3 within SEQ ID NO:5 (e.g., SEQ ID Nos. 6-8), SEQ ID NO:13 (e.g., SEQ ID Nos: 14-16), SEQ ID NO:21 (e.g., SEQ ID Nos: 22-24), SEQ ID NO:29 (e.g., SEQ ID Nos: 30-32), or SEQ ID NO:37 (e.g., SEQ ID NOS: 38-40) and/or at least 95%-100% sequence identity within CDRL1, CDRL2 and CDRL3 within SEQ ID NO:1 (e.g. SEQ ID Nos. 2-4), SEQ ID NO:9 (e.g., SEQ ID Nos: 10-12), SEQ ID NO: 17 (e.g., SEQ ID NOs. 18-20), SEQ ID NO:25 (e.g., SEQ ID Nos: 26-28), or SEQ ID NO: 33 (e.g., SEQ ID Nos: 34-36).

In one embodiment, the antibody or antigen binding fragment thereof has 100% sequence identity within CDRH1, CDRH2 and CDRH3 within SEQ ID NO:5 (e.g., SEQ ID Nos. 6-8), SEQ ID NO:13 (e.g., SEQ ID Nos: 14-16), SEQ ID NO:21 (e.g., SEQ ID Nos: 22-24), SEQ ID NO:29 (e.g., SEQ ID Nos: 30-32), or SEQ ID NO:37 (e.g., SEQ ID NOS: 38-40) and/or 100% sequence identity within CDRL1, CDRL2 and CDRL3 within SEQ ID NO: 1 (e.g.

SEQ ID Nos. 2-4), SEQ ID NO:9 (e.g., SEQ ID Nos: 10-12), SEQ ID NO:17 (e.g., SEQ ID NOs. 18-20), SEQ ID NO:25 (e.g., SEQ ID Nos: 26-28), or SEQ ID NO:33 (e.g., SEQ ID Nos: 34-36).

The polypeptide and nucleic acids described herein encompass those to which conservative modifications have been made. The terms "conservative modification" or "conservative sequence modification" refer to an amino acid modification that does not significantly alter the binding characteristics of an antibody or antibody fragment containing an amino acid sequence. Such conservative modifications include amino acid substitutions, additions and deletions. Modifications can be introduced into the antibodies or antibody fragments of the present invention by standard techniques known in the art, such as site-directed mutagenesis and PCR-mediated mutagenesis. Conservative amino acid substitutions are those in which the amino acid residue is replaced by an amino acid residue having a similar side chain. Families of amino acid residues having similar side chains have been defined in the related art. These families include, but are not limited to, basic side chains (e.g., lysine (Lys, L), arginine (Arg), histidine (His, H); acidic side chains (e.g., aspartic acid (Asp, D), glutamic acid (Glu, E)), uncharged polar side chains (e.g., asparagine (Asn, N), glutamine (Gln, Q), serine (Ser, S), threonine (Thr, T), tyrosine (Tyr, Y), nonpolar side chains (e.g., alanine (Ala, A), valine (Val, V), leucine (Leu, L), isoleucine (Ile, I), proline (Pro, P), phenylalanine (Phe, F), methionine (Met, M), Glycine (Gly, G), Cysteine (Cys, C)), beta-branched side chains (e.g., leucine (L), valine (V), isoleucine (I)). Thus, one or more amino acid residues within the antibody or antigen binding fragment thereof of the present invention may be replaced by other amino acid residues from the same side chain family, and the altered antibodies or antibody fragments thereof may be tested using the functional assays described herein. Suitably, conservative changes may even be made in the CDR region and not alter the functional binding of the antibody or antigen binding fragment thereof, which can be tested by the methods described herein.

Protein and nucleic acid sequence identities are evaluated using the Basic Local Alignment Search Tool ("BLAST") which is well known in the art (Karlin and Altschul, 1990, *Proc. Natl. Acad. Sci. USA* 87:2267-2268; Altschul et al., 1997, *Nucl. Acids Res.* 25:3389-3402). The BLAST programs identify homologous sequences by identifying similar segments, which are referred to herein as "high-scoring segment pairs," between a query amino or nucleic acid sequence and a test sequence which is known or obtained from a protein or nucleic acid sequence database. Preferably, the statistical significance of a high-scoring segment pair is evaluated using the statistical significance formula (Karlin and Altschul, 1990), the disclosure of which is incorporated by reference in its entirety. The BLAST programs can be used with the default parameters or with modified parameters provided by the user.

"Percentage of sequence "identity" or sequence "similarity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 75% sequence identity. Alternatively, percent identity can be any integer from 75% to 100%. More preferred embodiments include at least: 75%, 80%, 85%, 86%, 87%, 88%, 89%, 90%, 91%, 92%, 93%, 94%, 95%, 96%, 97%, 98% or 99% compared to a reference sequence using the programs described herein; preferably BLAST using standard parameters, as described. These values can be appropriately adjusted to determine corresponding identity of proteins encoded by two nucleotide sequences by taking into account codon degeneracy, amino acid similarity, reading frame positioning and the like.

"Substantial identity" of amino acid sequences for purposes of this invention normally means polypeptide sequence identity of at least 85%. Preferred percent identity of polypeptides can be any integer from 85% to 100%. More preferred embodiments include at least 85%, 86%, 87%, 88%, 89%, 90%, 91%, 92%, 93%, 94%, 95%, 96%, 97%, 98%, or 99%.

One may wish to express the antibodies or fragments of the present invention as a fusion protein with a pharmacologically or therapeutically relevant peptide. For example, one may wish to express an antibody with a protein linker and a protein therapeutic. Standard molecular biology techniques (e.g., restriction enzyme based sub-cloning, or homology based sub-cloning) could be used to place the DNA sequence encoding a protein therapeutic in frame with the targeting vector (usually a protein linker is also added to avoid steric hindrance). The fusion protein is then produced as one peptide in a host cell (e.g., yeast, bacteria, insect, or mammalian cell) and purified before use. Note the therapeutic does not need to be a whole protein. (For example, it can be a single peptide chain that is normally found as a subunit of a protein with more than one peptide. The other peptides can be co-expressed with the fusion protein and allowed to associate in the host cell or after secretion).

Further embodiments contemplated include antibody-drug conjugates. For example, suitable drugs may be conjugated to the antibodies or fragments described herein with a cleavable or non-cleavable linker. Cleavable and non-cleavable linkers are known in the art.

Conventional methods of linking a substance of interest to a polypeptide, in particular an antibody, are known in the art (e.g., See TERNYNCK and AVRAMEAS, 1987, "Techniques immunoenzymatiques" Ed. INSERM, Paris or G. T. Hermanson, Bioconjugate Techniques, 2010, Academic Press). For instance, many chemical cross-linking methods are also known in the art. Cross-linking reagents may be homobifunctional (i.e., having two functional groups that undergo the same reaction) or heterobifunctional (i.e., having two different functional groups). Numerous cross-linking reagents are commercially available and detailed instructions for their use are readily available from the commercial suppliers. A general reference on polypeptide cross-linking and conjugate preparation is: WONG, Chemistry of protein conjugation and cross-linking, CRC Press (1991).

In further embodiments, the antibody-conjugated agent is a therapeutic agent. As used herein, the term "therapeutic agent" refers to any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, chemotherapeutics, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, substances used for the treatment, prevention, diagnosis, cure or mitigation of a disease or illness; substances that affect the structure or function of the body, or pro-drugs, which become biologically active or more active after they have been placed in a physiological environment.

In some embodiments, the therapeutic agent is a chemotherapy agent. For example, in one embodiment, the antibody described herein is conjugated to a cytotoxic compound which is an antimitotic agent. In one specific embodiment, detailed in the Examples, the antibody is conjugated to the three to five units of the antimitotic agent monomethyl auristatin E (MMAE). Suitable methods of linking the antibody are known in the art and include, but are not limited to, for example, linkage with maleimide attachment groups, cathepsin cleavable linkers (valine-citrulline), and para-aminobenzylcarbamate spacers (FIG. 14, see, e.g., ADC Review/Journal of Antibody-drug Conjugates: Monomethyl auristatin E (MMAE), May 23, 2013, incorporated by reference in its entirety). The antibody is bound to the antimitotic agent stably as to not be easily released from the antibody under physiologic conditions to help prevent toxicity to healthy cells and ensure dosage efficiency. The conjugate may be rapidly and efficiently cleaved inside target tumor cell. The antibody portion of the drug attaches to CD30 on the surface of malignant cells, delivering MMAE which is responsible for the anti-tumor activity. Once bound, the conjugate is internalized by endocytosis and selectively taken up by targeted cancer cells.

In some embodiments, the antibodies to CD30 encompassed by the invention include mouse, human, chimeric or humanized antibodies and fragments thereof, including single chain antibodies, and such antibodies conjugated to therapeutic agents, for example, but not limited to, chemotherapeutic agents.

The term "single-chain variable fragment" or "scFv," as used herein, refers to a fusion protein of the variable regions of the heavy ($V_H$) and light chains ($V_L$) of immunoglobulins, connected with a short linker peptide of ten to about 25 amino acids. The linker may be rich in glycine for flexibility, as well as serine or threonine for solubility, and can either connect the N-terminus of the $V_H$ with the C-terminus of the $V_L$, or vice versa. This fusion protein may retain the specificity of the original immunoglobulin, despite removal of the constant regions and the introduction of the linker. scFvs are often be produced in microbial cell cultures such as *E. coli* or *Saccharomyces cerevisiae*. Suitable scFvs of the present invention comprise, consist or consist essentially of: (a) a light chain variable domain comprising a CDRL1 region of SEQ ID NO:2, a CDRL2 region of SEQ ID NO:3, and a CDRL3 region of SEQ ID NO:4 linked to a heavy chain variable domain comprising a CDRH1 region of SEQ ID NO:6, a CDRH2 region of SEQ ID NO:7, and a CDRH3 region of SEQ ID NO:8; (b) a light chain variable domain comprising a CDRL1 region of SEQ ID NO:10, a CDRL2 region of SEQ ID NO:11, and a CDRL3 region of SEQ ID NO:12 linked to a heavy chain variable domain comprising a CDRH1 region of SEQ ID NO:14, a CDRH2 region of SEQ ID NO: 15, and a CDRH3 region of GAY, (c) a light chain variable domain comprising a CDRL1 region of SEQ ID NO:18, a CDRL2 region of SEQ ID NO:19, and a CDRL3 region of SEQ ID NO: 20 linked to a heavy chain variable domain comprising a CDRH1 region of SEQ ID NO: 22, a CDRH2 region of SEQ ID NO:23, and a CDRH3 region of SEQ ID NO:24, (d) a light chain variable domain comprising a CDRL1 region of SEQ ID NO:26, a CDRL2 region of SEQ ID NO:27, and a CDRL3 region of SEQ ID NO:28 linked to a heavy chain variable domain comprising a CDRH1 region of SEQ ID NO:30, a CDRH2 region of SEQ ID NO:31, and a CDRH3 region of SEQ ID NO:32, or (e) a light chain variable domain comprising a CDRL1 region of SEQ ID NO:34, a CDRL2 region of SEQ ID NO:35, and a CDRL3 region of SEQ ID NO:36 linked to a heavy chain variable domain comprising a CDRH1 region of SEQ ID NO:38, a CDRH2 region of SEQ ID NO:39, and a CDRH3 region of SEQ ID NO:40. Alternatively the scFv comprises, consists, or consists essentially of a light and a heavy chain that have substantial identity to the polypeptide sequences found in SEQ ID NOs: 1 and 5; 9 and 13; 17 and 21; 25 and 29; 33 and 37 respectively, or substantial identity in the CDR regions within the heavy and light chain of the antibody or antigen-binding fragment thereof as described herein. Suitably the scFv comprises the heavy chain and light chain attached by a linker where the linker is a short amino acid sequence that allows for the flexibility between the heavy and light chains to produce a functional antigen binding site on the molecule. Suitable examples of scFv are found in SEQ ID NO:41-52 (both nucleic acids encoding the scFv and the protein sequence of the ScFv are provided). In one embodiment, the scFv is an amino acid sequence of any one of SEQ ID NO: 42, 44, 46, 48, 50 or 52.

The present invention provides chimeric antigen receptor (CAR) comprising a CD30 binding domain, derived from the antibodies, antibody fragments, and scFvs disclosed herein. CARs are receptor proteins that are expressed at the surface of immune effector cells to target the cells to a specific protein. CAR receptors are fusion proteins that combine a specific antigen-binding peptide with a cell activating receptor. For example, the CARs of the present invention may be used to generate CD30-specific T cells which can be used to target CD30+ cancer cells.

CARs typically include (1) an extracellular domain, (2) a transmembrane domain and (3) an intracellular signaling domain. The extracellular domain may include an antigen binding domain that binds to a specific antigen (e.g., a tumor antigen or CD30). The CARs provided with the present invention have an antigen binding region that comprises a CD30 binding antibody or antigen binding fragment thereof, as described herein. In certain embodiments, the CARs comprise a scFv, as exemplified in SEQ ID NO:42, 44, 46, 48, 50 and 52 (DNA encoding the scFv found in SEQ ID NO:41, 43, 45, 47, 49, and 51, respectively) attached the transmembrane and intercellular signaling domain. Suitable transmembrane and intercellular signaling domain are known in the art, and include, for example, SEQ ID NO:56 (encoded by nucleic acid SEQ ID NO:55). The extracellular domain can also include a signal peptide that directs the nascent protein into the endoplasmic reticulum. Signal peptide can be essential if the CAR is to be glycosylated and anchored in the cell membrane. A suitable example of a CAR of the present invention is shown in SEQ ID NO:54 (nucleic acid sequence SEQ ID NO:53), however similar CAR may be made using the other scFv and transmembrane and intercellular domain of SEQ ID NO:56. Thus, examples of CAR amino acid sequences contemplate herein include, but are not limited to, for example, (a) SEQ ID NO:42 (scFv)-linker-SEQ ID NO:56; (b) SEQ ID NO:44-linker- SEQ ID NO:56, (c) SEQ ID NO:46-linker-SEQ ID NO:56; (d) SEQ ID NO:48-linker-SEQ ID NO:56; (e) SEQ ID NO:50-linker-SEQ ID NO: 56; or (f) SEQ ID NO:52-linker-SEQ ID NO:56. Linkers can be designed by one skilled in the art and include those contemplated herein including 10-25 amino acids, preferably rich in glycines.

The transmembrane domain anchors the CAR to the effector cell and functionally links the extracellular domain to the intracellular domain. The transmembrane domain is typically a hydrophobic alpha helix that spans the membrane. Different transmembrane domains result in differential receptor stability. The transmembrane domain of the CAR can include, for example, a CD3ζ polypeptide, a CD4 polypeptide, a CD8 polypeptide, a CD28 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, and a BTLA polypeptide, which are known in the art.

After antigen recognition, the intracellular signaling domain of the CAR transmits an activation signal to the cell (Eshhar, (1993); Altenschmidt (1999)). In some embodiments, the signaling domain is derived from CD3ζ or FcRγ. In certain embodiments, one or more costimulatory domains are included in the intracellular domain to provide improved T cell activation. As used herein, "costimulatory domains" refer to cell surface molecules other than antigen receptors or their ligands that are required for an efficient response of lymphocytes to an antigen. Exemplary costimulatory molecules include a CD28 polypeptide, a CD134 polypeptide, a CD278 polypeptide, a 4-IBB polypeptide (also known as CD137), an OX40 polypeptide, an ICOS polypeptide, a DAP-10 polypeptide, a PD-1 polypeptide, a LAG-3 polypeptide, a 2B4 polypeptide, a BTLA polypeptide, or a CTLA-4 polypeptide. In some embodiments, the intracellular domain of the CAR comprises more than one costimulatory domain.

Engagement of the CAR with its target antigen or cell results in the clustering of the CAR and delivers an activation stimulus to the CAR-containing effector cell. The main characteristic of the CARs is their ability to redirect immune effector cell specificity, thereby triggering proliferation, cytokine production, phagocytosis and production of molecules that can mediate cell death of the target cell in a major histocompatibility (MHC) independent manner, exploiting the cell specific targeting ability of antibodies.

Optionally, a hinge region (also referred to as a spacer region) may be incorporated between the extracellular domain and the transmembrane domain of the CAR, or between the cytoplasmic domain and the transmembrane domain of the CAR. As used herein, a hinge region generally refers to any oligo- or polypeptide that functions to link the transmembrane domain to either the extracellular domain or the cytoplasmic domain in the polypeptide chain. A hinge region may comprise up to 300 amino acids, preferably about 10-100 amino acids, alternatively about 25-50 amino acids. The hinge region may be flexible, for example to allow the antigen binding domain to orient in different directions to facilitate antigen recognition.

Any CARs that are suitable for engineering effector cells (e.g., T cells, NK cells, or NKT cells) for use in adoptive immunotherapy therapy can be used in the present invention.

There are four main classes or "generations" of CARS. "First generation" CARs are typically composed of an antibody derived antigen recognition domain (e.g., a scFv) fused to a transmembrane domain, fused to cytoplasmic signaling domain of the T cell receptor chain. First generation CARs typically have the intracellular domain from the CD3 g-chain, which is the primary transmitter of signals from endogenous TCRs. "Second generation" CARs add intracellular signaling domains from various costimulatory protein receptors (e.g., CD28, 41BB, ICOS, OX40) to the cytoplasmic tail of the CAR to provide additional signals to the T cell. "Third generation" CARs combine multiple costimulatory domains, such as CD28-41BB or CD28-OX40, to augment T cell activity. "Fourth generation" CARs (also known as TRUCKs or armored CARs) include additional factors that enhance T cell expansion, persistence, and anti-tumoral activity. This can include cytokines, such is IL-2, IL-5, IL-12 and costimulatory ligands. Suitable CARs include those described in Sadelain, et al., "The Basic Principles of Chimeric Antigen Receptor Design." Cancer Discovery, OF1-11, (2013), Chicaybam, et al., (2011), Brentjens et al. Nature Medicine 9:279-286 (2003), and U.S. Pat. No. 7,446,190, which are herein incorporated by reference in their entireties. Non-limiting examples of suitable CARs include, but are not limited to, CD19-targeted CARs (see U.S. Pat. No. 7,446,190; United States Patent Application Publication No. 2013/0071414), HER2-targeted CARs (see Ahmed, et al., Clin Cancer Res., 2010), MUC16-targeted CARs (see Chekmasova, et al., 2011), prostate-specific membrane antigen (PSMA)-targeted CARs (for example, Zhong, et al., Molecular Therapy, 18 (2): 413-420 (2010), all of which are herein incorporated by reference in their entireties. Exemplary CARs are provided in SEQ ID NO:54 (DNA sequence SEQ ID NO:55), but other exemplary CARs with the other scFvs are also included within the scope of the invention (e.g. CARs containing scFvs any one of SEQ ID NOs: 42, 44, 46, 48, 50 or 52.)

Other suitable ON-switch chimeric antigen receptors (CAR) are also contemplated in the present invention. For example, small molecule-gated CAR are contemplated, as described in Wu et al. ("Remote control of therapeutic T cells through a small molecule-gated chimeric receptor" Science 350 (6258), Oct. 16, 2015, aab4077-9, incorporated by reference in its entirety).

Suitable CARs include CubiCAR, a tri-functional CAR architecture that enables CAR-T cell detection, purification and on-demand depletion using CD20 minitopes and CD34 epitopes for T cell depletion and enrichment, respectively, as described in Valton et al. ("A Versatile Safeguard for Chimeric Antigen Receptor T-cell Immunotherapies" Nature Scientific Reports 8, Article number: 8972 (2018), the contents of which are incorporated by reference in its entirety.)

Suitable methods of making a CAR are described in, for example, US Appl. Publ. No. 2013/0287748, and PCT Appl. Publ. No. WO 2140099671, the contents of which are incorporated by reference in their entireties.

In another embodiment, the invention provides a nucleic acid or nucleic acid construct encoding the CARs disclosed herein.

The present invention also provides genetically modified immune effector cells comprising the CARs disclosed herein. Suitable effector cells include T lymphocytes, natural killer (NK) cells, natural killer T (NKT) cells, and mature immune effector cells including neutrophils and macrophages (which upon administration in a subject differentiate into mature immune effector cells). In preferred embodiments, the effector cells are T cells. CAR-expressing immune effector cells are capable of killing target cells by effector cell mediated (e.g. T cell-mediated) cell death. In the case of T cell mediated killing, CAR-target binding initiates CAR signaling to the T cell, resulting in activation of a variety of T cell signaling pathways that induce the T cell to produce or release proteins capable of inducing target cell apoptosis by various mechanisms. These T cell mechanisms include, but are not limited to, for example, the transfer of intracellular cytotoxic granules from the T cell into the target cell, T cell secretion of pro-inflammatory cytokines that can induce target cell killing directly or indirectly via recruitment of other killer effector cells, and upregulation of death receptor ligands on the T cell surface that induce target cell apoptosis following binding to their cognate death receptor on the target cell. Further embodiments provide an isolated nucleic acid molecule that encodes for the antibodies or antigen binding fragment thereof described above. As used herein, term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

A recombinant expression cassette comprising a polynucleotide encoding the antibody or antigen binding fragment thereof of the present invention is also contemplated. The polynucleotide may be under the control of a transcriptional promoter allowing the regulation of the transcription of said polynucleotide in a host cell. Said polynucleotide can also be linked to appropriate control sequences allowing the regulation of its translation in a host cell.

The present invention also provides expression vectors comprising a polynucleotide encoding the antibodies or fragments of the present invention. Advantageously, the expression vector is a recombinant expression vector comprising an "expression cassette" or an "expression construct" according to the present invention. Within the construct, the polynucleotide may operatively linked to a transcriptional promoter (e.g., a heterologous promoter) allowing the construct to direct the transcription of said polynucleotide in a host cell. Such vectors are referred to herein as "recombinant constructs," "expression constructs," "recombinant expression vectors" (or simply, "expression vectors" or "vectors").

Suitable vectors are known in the art and contain the necessary elements in order for the gene encoded within the vector to be expressed as a protein in the host cell. The term "vector" refers to a nucleic acid molecule capable of transporting another nucleic acid to which it has been linked. One type of vector is a "plasmid", which refers to a circular double stranded DNA loop into which additional DNA segments may be ligated, specifically exogenous DNA segments encoding the antibodies or fragments thereof. Another type of vector is a viral vector, wherein additional DNA segments may be ligated into the viral genome. Certain vectors are capable of autonomous replication in a host cell into which they are introduced. Other vectors can be integrated into the genome of a host cell upon introduction into the host cell, and thereby are replicated along with the host genome (e.g. lentiviral vectors). Vector includes expression vectors, such as viral vectors (e.g., replication defective retroviruses (including lentiviruses), adenoviruses and adeno-associated viruses (rAAV)), which serve equivalent functions.

Lentiviral vectors may be used to make suitable lentiviral vector particles by methods known in the art to transform cells in order to express the antibody or antigen binding fragment thereof described herein. The present invention also provides a host cell comprising the isolated nucleic acids or expression vectors described herein. In one embodiment, the host cell is a hybridoma cell. In another embodiment, the host cell contains a recombinant expression cassette or a recombinant expression vector according to the present invention and is able to express the encoded antibody or antigen binding fragment thereof. The host cell can be a prokaryotic or eukaryotic host cell. Suitable host cells include, but are not limited to, mammalian cells, bacterial cells and yeast cells. In some embodiments, the host cell may be a eukaryotic cell. The term "host cell" includes a cell into which exogenous nucleic acid has been introduced, including the progeny of such cells. Host cells also include "transformants" and "transformed cells", which include the primary transformed cell and progeny derived therefrom without regard to the number of passages. Progeny may not be completely identical in nucleic acid content to a parent cell, but may contain mutations. Mutant progeny that have the same function or biological activity that was screened or selected for in the originally transformed cell are included herein. It should be appreciated that the host cell can be any cell capable of expressing antibodies, for example fungi; mammalian cells; insect cells, using, for example, a baculovirus expression system; plant cells, such as, for example, corn, rice, *Arabidopsis*, and the like. See, generally, Verma, R. et al., *J Immunol Methods*. 1998 Jul. 1; 216(1-2):165-81. Host cell also include hybridomas that produce the monoclonal antibodies described herein.

In one embodiment, the host cell is a hybridoma cell.

The antibodies or antibody fragments can be wholly or partially synthetically produced. Thus the antibody may be from any appropriate source, for example recombinant sources and/or produced in transgenic animals or transgenic plants. Thus, the antibody molecules can be produced in vitro or in vivo. Preferably the antibody or antibody fragment comprises at least the heavy chain variable region ($V_H$) which generally comprises the antigen binding site. In preferred embodiments, the antibody or antibody fragment comprises the heavy chain variable region and light chain variable region ($V_L$). The antibody or antibody fragment can be made that comprises all or a portion of a heavy chain constant region, such as an IgG1, IgG2, IgG3, IgG4, IgA1, IgA2, IgE, IgM or IgD constant region.

Furthermore, the antibody or antibody fragment can comprise all or a portion of a kappa light chain constant region or a lambda light chain constant region. All or part of such constant regions may be produced wholly or partially synthetic. Appropriate sequences for such constant regions are well known and documented in the art.

In some embodiments, the disclosure provides a composition comprising the isolated antibody or antigen binding fragment thereof specific for human CD30. In a preferred embodiment, the composition further includes a suitable carrier, preferably a pharmaceutically acceptable carrier. Compositions are provided that include one or more of the disclosed antibodies. Compositions comprising antibodies or antigen binding fragments thereof that are conjugated to and/or directly or indirectly linked to an agent are also provided. The compositions can be prepared in unit dosage forms for administration to a subject. The amount and timing of administration are at the discretion of the treating clinician to achieve the desired outcome. The antibody can be formulated for systemic or local (such as intravenous, intrathecal) administration.

As used herein, "pharmaceutical composition" means therapeutically effective amounts of the antibody together with a pharmaceutically-acceptable carrier. "Pharmaceutically acceptable" carriers are known in the art and include, but are not limited to, for example, suitable diluents, preservatives, solubilizers, emulsifiers, liposomes, nanoparticles and adjuvants. Pharmaceutically acceptable carriers are well known to those skilled in the art and include, but are not limited to, 0.01 to 0.1 M and preferably 0.05 M phosphate buffer or 0.9% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include isotonic solutions, alcoholic/aqueous solutions, emulsions or suspensions, including saline and buffered media.

Pharmaceutical compositions of the present disclosure may include liquids or lyophilized or otherwise dried formulations and may include diluents of various buffer content (e.g., Tris-HCl, acetate, phosphate), pH and ionic strength, additives such as albumin or gelatin to prevent absorption to surfaces, detergents (e. g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, milamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

In some embodiments, the compositions comprise a pharmaceutically acceptable carrier, for example, buffered saline, and the like. The compositions can be sterilized by conventional, well known sterilization techniques. The compositions may contain pharmaceutically acceptable additional substances as required to approximate physiological conditions such as a pH adjusting and buffering agent, toxicity adjusting agents, such as, sodium acetate, sodium chloride, potassium chloride, calcium chloride, sodium lactate, and the like.

In some embodiments, the antibodies are provided in lyophilized form and rehydrated with sterile water or saline solution before administration. In some embodiments, the antibodies are provided in sterile solution of known concentration. In some embodiments, the antibody composition may be added to an infusion bag containing 0.9% sodium chloride, USP and in some cases, administered in a dosage of from 0.5 to 15 mg/kg of body weight.

One embodiment of the present invention provides a method of treating a patient having a CD30+ cancer, the method comprising administering a therapeutically effective amount of the isolated antibody or antigen binding fragment thereof capable of binding human CD30 as described herein to treat the cancer.

For purposes of the present invention, "treating" or "treatment" describes the management and care of a subject for the purpose of combating the disease, condition, or disorder. Treating includes the administration of an antibody of present invention to prevent the onset of the symptoms or complications, alleviating the symptoms or complications, or eliminating the disease, condition, or disorder.

The term "treating" can be characterized by one or more of the following: (a) the reducing, slowing or inhibiting the growth of cancer, including reducing slowing or inhibiting the growth of cancer cells; (b) preventing the further growth of tumors; (c) reducing or preventing the metastasis of cancer within a patient, and (d) reducing or ameliorating at least one symptom of the cancer. In some embodiments, the optimum effective amounts can be readily determined by one of ordinary skill in the art using routine experimentation.

In another embodiment, the treatment can result in cell-cycle inhibition of tumor cells (i.e. cytostasis). Cell cycle inhibition may be achieved, for example, by conjugating the antibody of the present invention to CDK4/6 inhibitors.

As used herein, the terms "effective amount" and "therapeutically effective amount" refer to the quantity of active therapeutic agent or agents sufficient to yield a desired therapeutic response without undue adverse side effects such as toxicity, irritation, or allergic response. The specific "effective amount" will, obviously, vary with such factors as the particular condition being treated, the physical condition of the subject, the type of animal being treated, the duration of the treatment, the nature of concurrent therapy (if any), and the specific formulations employed and the structure of the compounds or its derivatives.

In some embodiments, the antibody of the present invention is used for treatment in addition to standard treatment options, for example surgery and radiation therapy. In some embodiments, the antibodies of the present disclosure are used in combination therapy, e.g. therapy including one or more different anti-cancer agents.

Suitable CD30+ cancers include, hematologic malignancies, for example, Hodgkins lymphoma, anaplastic large cell lymphoma, acute myeloid leukemia (AML), ovarian cancer, mesothelioma, skin squamous cell carcinoma, triple negative breast cancer, pancreatic cancer, small cell lung cancer, anal cancer, and thyroid carcinoma, among others. CD30 has also been shown to be expressed on a subset of non-Hodgkin's lymphomas (NHL), including Burkitt's lymphoma, anaplastic large-cell lymphomas (ALCL), cutaneous T-cell lymphomas, nodular small cleaved-cell lymphomas, lymphocytic lymphomas, peripheral T-cell lymphomas, Lennert's lymphomas, immunoblastic lymphomas, T-cell leukemia/lymphomas (ATLL), adult T-cell leukemia (T-ALL), and entroblastic/centrocytic (cb/cc) follicular lymphomas, along with embryonal carcinomas, nonembryonal carcinomas, malignant melanomas, and mesenchymal tumors. As such, the present methods may be used to treat any cancer in which CD30+ tumor cells are found.

In another embodiment, the present disclosure provides a method of inhibiting growth of a tumor cell expressing CD30, comprising contacting the tumor cell with an effective amount of the antibody or antigen binding fragment thereof such that the growth of the cell is inhibited. In some embodiments, the antibody is conjugated to a drug or therapeutic.

In some embodiments of the present invention, antibodies or antigen binding fragments thereof may be administered with or without modifications. One may wish to administer the antibodies of the present invention without the modifications described above. For example, one may administer the antibodies through an intravenous injection or through intra-peritoneal and subcutaneous methods.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, intraaural administration, rectal administration, sublingual administration, buccal administration, and parenteral administration, including injectable such as intravenous administration, intra-arterial administration, intramuscular administration, intradermal administration, intrathecal administration and subcutaneous administration. Administration can be continuous or intermittent. In various aspects, a preparation can be administered therapeutically; that is, administered to treat an existing disease or condition. In a preferred embodiment, the administration is intravenous administration.

In some embodiments, the antibodies of the invention specifically bind CD30 and exert cytostatic and cytotoxic effects on malignant cells in cancer (e.g., Hodgkin's lymphoma).

Another embodiment provides methods and kits of assaying the presence of CD30+ cancer cells within a sample. The method comprises contacting the sample with the antibody specific to CD30 described herein and detecting the presence of binding. Suitable methods of detection are known in the art, including, for example, but not limited to, flow cytometry, ELISA, Western Blot, and immunohistochemistry.

In another embodiment, the CD30 antibodies of the present invention may be used to stratify patients into risk groups. CD30 is a tumor antigen expressed on a subset of AML patients, and may be associated with high-risk disease. CD30 mAbs can therefore be used diagnostically, to stratify patients into risk groups.

In one embodiment, the disclosure provides a method of detecting CD30$^+$ cells within a sample from a subject, the method comprising contacting the sample with the CD30$^-$ antibody described herein and determining the amount of binding of the antibody to cells within the sample. In one embodiment, the subject is a patient with or suspected of having AML. In another embodiment, the subject is a patient with or suspected of having Hodgkin's lymphoma. In some embodiments, the patients are classified or categorized by the level of CD30 detected on the tumor cell surface.

In some embodiments, kits for carrying out the methods described herein are provided. The kits provided may contain the necessary components with which to carry out one or more of the above-noted methods. In one embodiment, a kit for detecting CD30$^+$ cells within a sample is provided. The kit comprises a CD30– antibody described herein and instructions for use. In some embodiments, the antibody is conjugated to a detection agent or magnetic beads. In further embodiments, a control is provided. In one embodiment, the control is a positive control, for example, CD30$^+$ cells.

In another embodiment, kits for treating a subject with a CD30$^+$ cancer are provided. The kit comprises a CD30– antibody described herein and instructions for use. In some embodiments, the antibody is conjugated to a therapeutic or drug, for example, but not limited to, a chemotherapeutic drug. Further, the kit may comprise a pharmaceutically acceptable carrier and instructions for use.

The present invention has been described in terms of one or more preferred embodiments, and it should be appreciated that many equivalents, alternatives, variations, and modifications, aside from those expressly stated, are possible and within the scope of the invention.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim. For example, with regard to sequences "consisting of" refers to the sequence listed in the SEQ ID NO. and does refer to larger sequences that may contain the SEQ ID as a portion thereof.

The invention will be more fully understood upon consideration of the following non-limiting examples.

The present invention has been described in terms of one or more preferred embodiments, and it should be appreciated that many equivalents, alternatives, variations, and modifications, aside from those expressly stated, are possible and within the scope of the invention.

EXAMPLES

Example 1: Anti-CD30 Monoclonal Antibody Production

Figure 2:
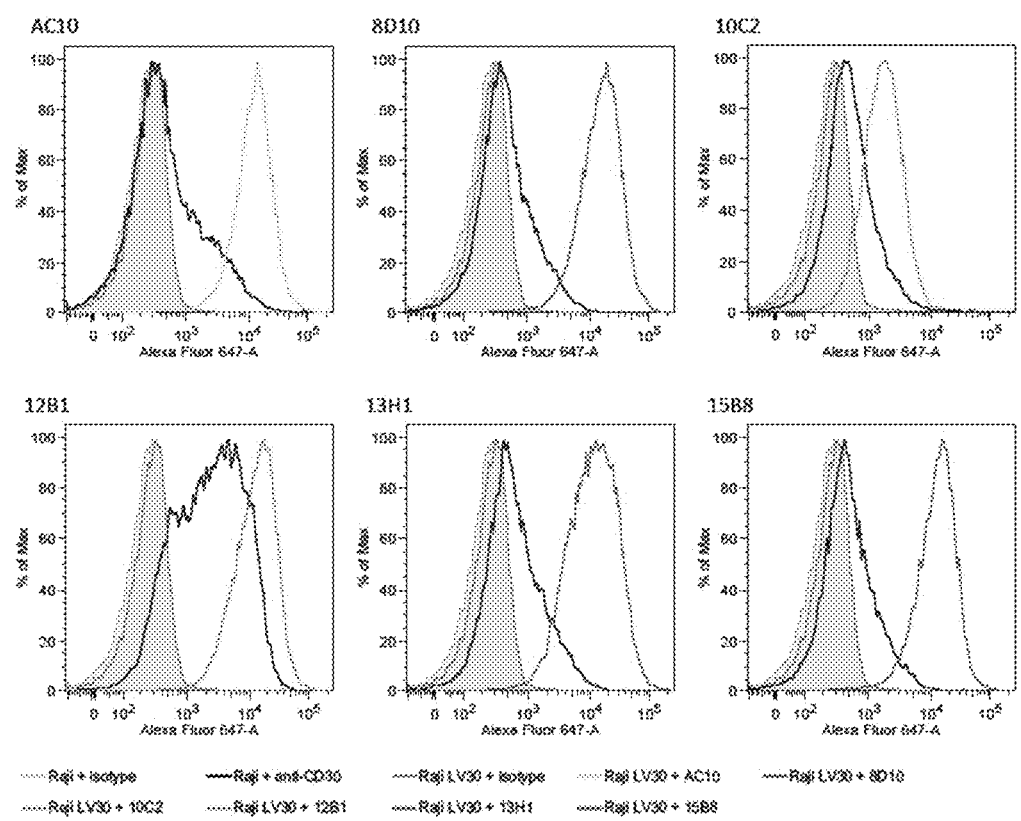
FIG. 2 depicts specific binding of the CD30 antibodies using flow cytometry on non-transduced Raji (low levels of endogenous CD30 expression) and LV transduced CD30+ Raji cells (high levels of CD30 expression).

We have employed hybridoma technology to generate novel murine anti-human CD30 mAbs. Mice were immunized and boosted with purified human GST-tagged CD30. Mouse spleen cells were then harvested and fused with myeloma cells to generate antibody secreting hybridoma. Hybridoma supernatants were screened for specificity to purified CD30 protein by ELISA, and GST specific clones were eliminated. Fifteen anti-human CD30 hybridoma cell lines were made, five were selected for further analysis. Specific binding of our mAbs to cell-surface expressed CD30 was assessed by flow cytometry (FIG. 1) using 293T cells (CD30–), lentiviral transduced 293T cells expressing huCD30, and K562 cells which are naturally CD30+. The 293T (CD30–), 293T LV huCD30 (transduced with human CD30), SU-DHL-1 (lymphoma), RPMI.6666 (lymphoma) or K562 (CML) cell lines were incubated with each antibody in the form of unpurified hybridoma supernatant, and then incubated with an Alexa Fluor 647-labeled anti-mouse IgG antibody. Cell-associated fluorescence was determined by FACS. FIG. 2 demonstrates binding of purified antibodies to cells with CD30 surface expression.

Each of five hybridoma clones, designated as 8D10, 10C2, 12B1, 13H1, and 15B8, bound to CD30+ but not CD30– cell lines indicating specificity for the selected antigen. See FIGS. 1 and 2.

All candidates show specific binding to CD30 and have been DNA and protein sequenced. The percentage identity between the heavy and light chains of the monoclonal antibodies selected were compared with the results shown in FIG. 3A and FIG. 3B.

CD30 mAb Binding-ELISA

Figure 4:
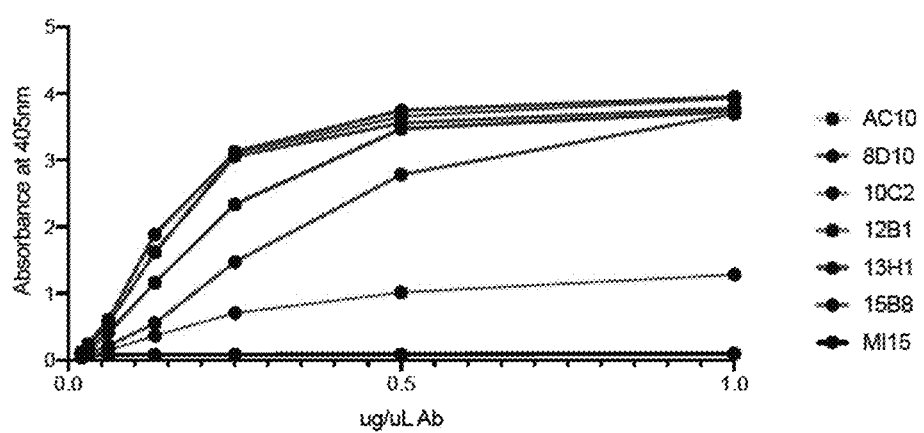
FIG. 4 depicts the binding of the antibodies to CD30 as measured by ELISA.
Figure 5:
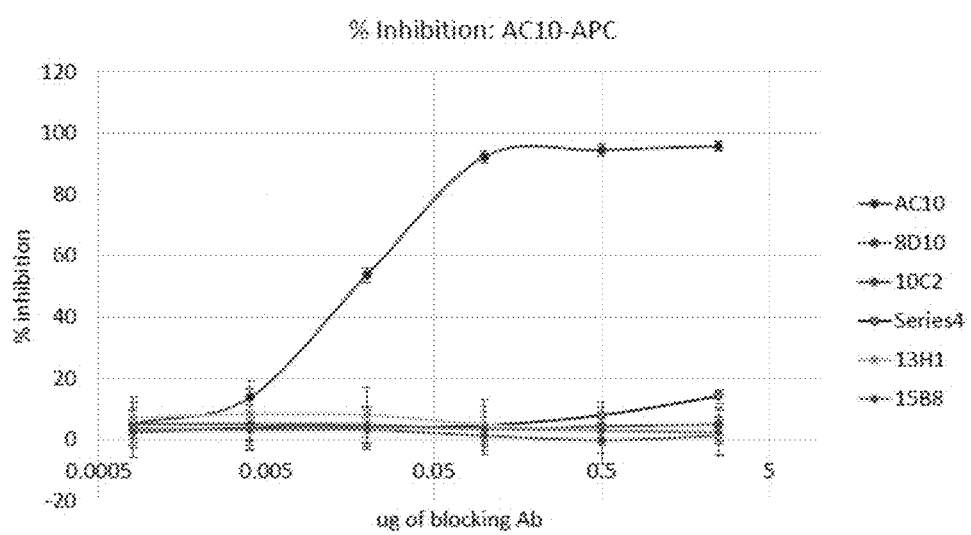
FIG. 5 depicts the percent inhibition of AC10 binding to CD30$^+$ cells (SU-DHL-1 cells) by 8D10, 10C2, 12B1, 13H1, 15B8, or AC10 antibodies.
Figure 6:
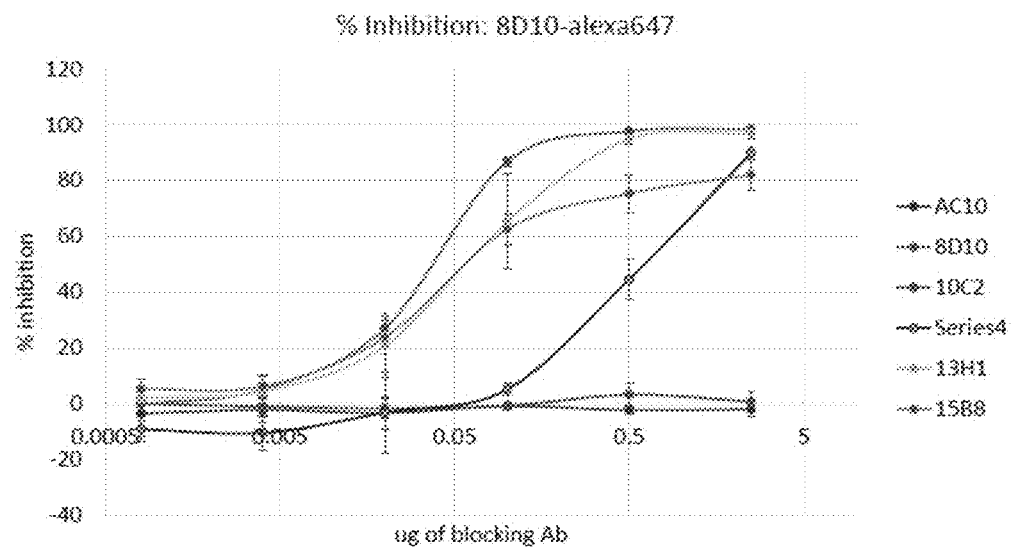
FIG. 6 depicts the percent inhibition of 8D10 binding to CD30$^+$ cells (SU-DHL-1 cells) by 8D10, 10C2, 12B1, 13H1, 15B8, or AC10 antibodies.
Figure 7:
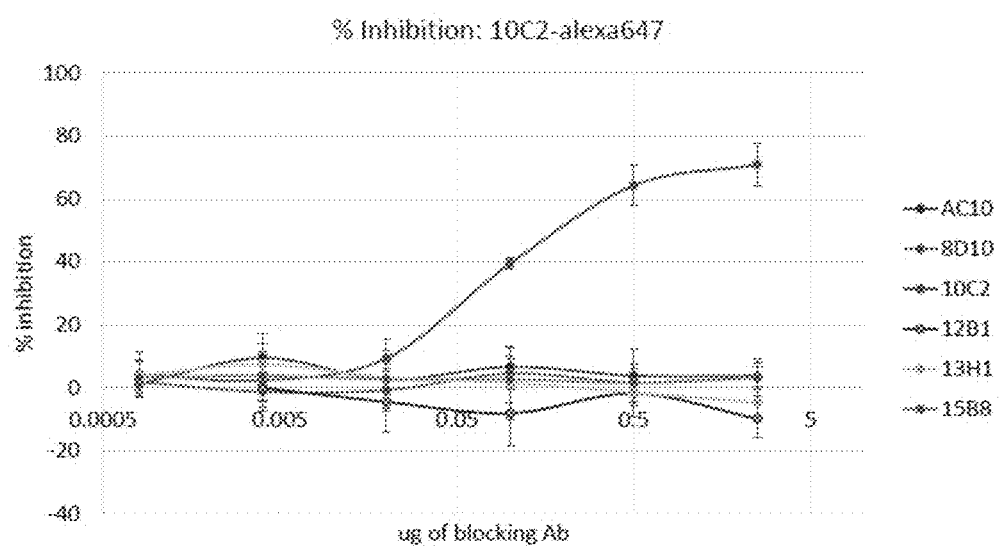
FIG. 7 depicts the percent inhibition of 10C2 binding to CD30$^+$ cells (SU-DHL-1 cells) by 8D10, 10C2, 12B1, 13H1, 15B8, or AC10 antibodies.
Figure 8:
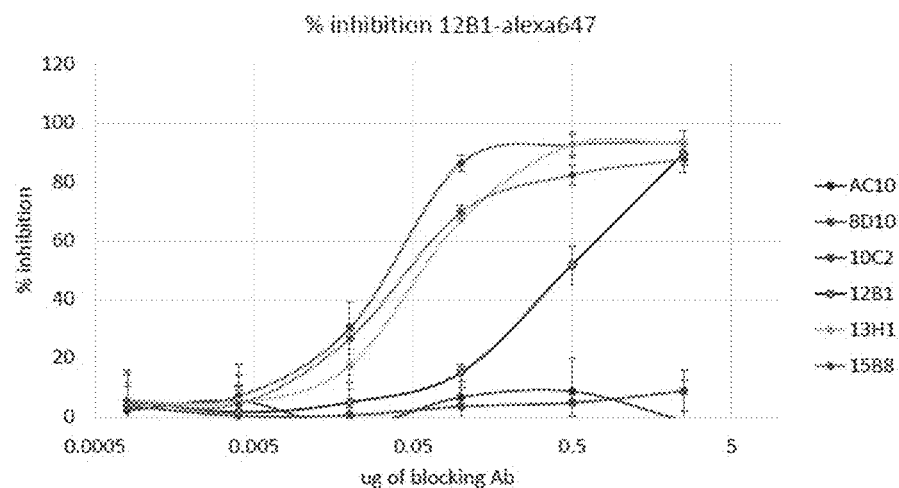
FIG. 8 depicts the percent inhibition of 12B1 binding to CD30$^+$ cells (SU-DHL-1 cells) by 8D10, 10C2, 12B1, 13H1, 15B8, or AC10 antibodies.
Figure 9:
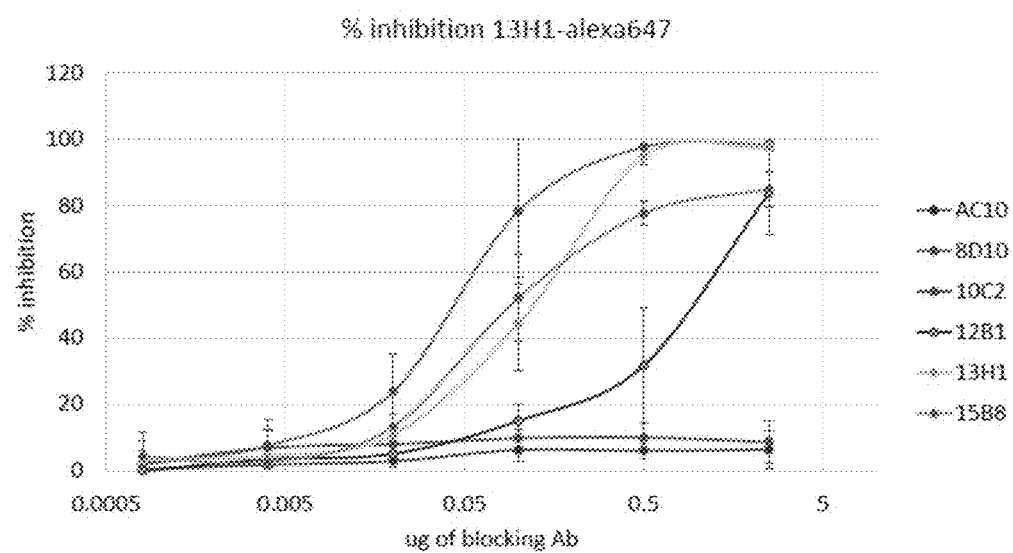
FIG. 9 depicts the percent inhibition of 13H1 binding to CD30$^+$ cells (SU-DHL-1 cells) by 8D10, 10C2, 12B1, 13H1, 15B8, or AC10 antibodies.
Figure 10:
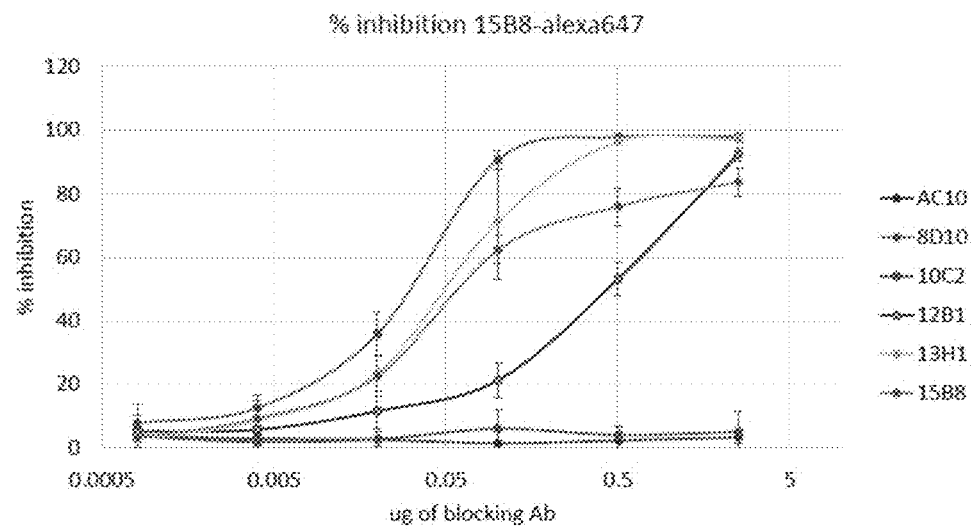
FIG. 10 depicts the percent inhibition of 15B8 binding to CD30$^+$ cells (SU-DHL-1 cells) by 8D10, 10C2, 12B1, 13H1, 15B8, or AC10 antibodies.

Microtiter plates were coated with recombinant CD30-GST fusion protein. Wells were blocked with 5% bovine serum albumin (BSA) solution. Purified 8D10, 10C2, 12B1, 13H1, 15B8, BY88 (commercial anti-CD30 antibody), AC10 (commercial anti-CD30 antibody) or MI15 (commercial anti-CD138 antibody) were added and incubated at varying concentrations. Wells were detected by incubating with an alkaline phosphatase-labeled anti-mouse IgG antibody. The plate was developed with pNPP (p-nitrophenyl phosphate). The optical density at 405 was determined using a plate reader and the results are shown in FIG. 4.

CD30 Mab Epitope Studies.

Figure 11:
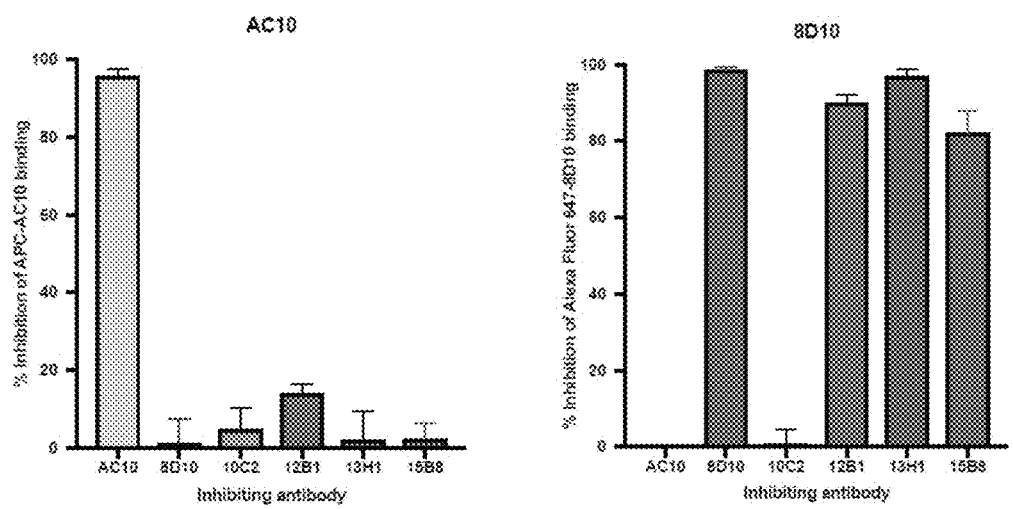
FIG. 11 is a set of bar graphs summarizing the blocking ability of the antibodies to AC10 (left) and 8D10 (right) binding to CD30$^+$ cells.
Figure 12:
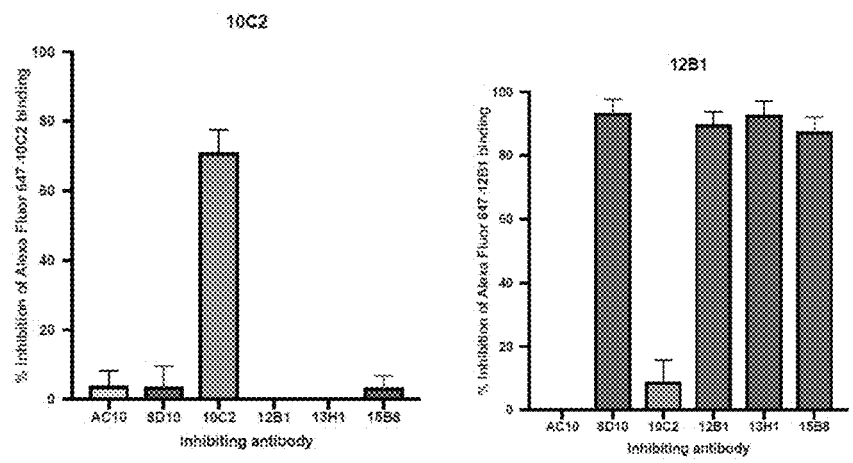
FIG. 12 is a set of bar graphs summarizing the blocking ability of the antibodies to 10C2 (left) and 12B1 (right) binding to CD30$^+$ cells.
Figure 13:
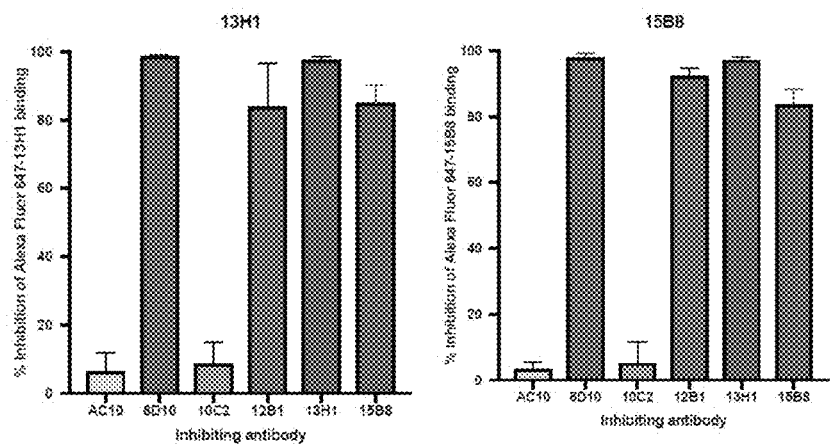
FIG. 13 is a set of bar graphs summarizing the blocking ability of the antibodies to 13H1 (left) and 15B8 (right) binding to CD30$^+$ cells.

CD30+ SU-DHL-1 cells were blocked with unlabeled 8D10, 10C2, 12B1, 13H1, 15B8, or AC10 at 6 serial dilutions. The blocked cells were then incubated with fluorescently-labeled 8D10, 10C2, 12B1, 13H1, 15B8, or AC10. Excess labelled antibody was washed from the cells, and the cell-associated fluorescence was determined by FACS. Data is shown as a curve, plotted against increasing concentrations of blocking ab (FIG. 5-10), and as a bar graph showing that values at the maximum concentration (2.5 ug) of blocking antibody (FIG. 11-13).

All five antibodies have unique light and heavy chain sequences. These sequences also differ from the FDA-approved anti-CD30 antibody AC10 (Brentuximab vedotin). All five antibodies bind to CD30, as indicated by FACS and ELISA assays. All five antibodies bind to an epitope that is different from AC10 (Brentuximab). 8D10, 12B1, 13H1, 15B8 bind to the same or similar epitope as each other while 10C2 binds to an epitope that is distinct both from AC10, and from the other four novel antibodies reported here.

All antibodies bind an epitope distinct from Brentuximab vedotin.

Each publication, patent, and patent publication cited in this disclosure is incorporated in reference herein in its entirety. The present invention is not intended to be limited to the foregoing examples, but encompasses all such modifications and variations as come within the scope of the appended claims.

```
Anti-CD30 mAb CDR
8D10-Light chain
                                        (SEQ ID NO: 1)
DIVMTQSPASQSASLGESVTITCLASQTIGTWLAWYQQKPGKSPQFLIY

AATSLADGVPSRF SGSGSGTKFSFKISSLQAEDFVSYYC

QQLYSTPFTFGGGTKLEIK
(CDRL1-SEQ ID NO: 2-underline; CDRL2-SEQ ID NO: 3-
bold; CDRL3-SEQ ID NO: 4-bold/underline)

8D10-Heavy chain
                                        (SEQ ID NO: 5)
QVQLQESGTELVKPGASVKLSCKASGYTFTSYWMHWMKQRPGQGLEWIGN

INPSNGGTNYNEKFKNKATLTVDKSSSTAYMQLSSLTSEDSAVYYCAR

RDYYYGSSYGFDVWGTGTTVTVSS
(CDH1-SEQ ID NO: 6-underline; CDH2-SEQ ID NO: 7-
bold; CDH3-SEQ ID NO: 8-bold/underline)

10C2-Light chain
                                        (SEQ ID NO: 9)
DIVLTQTPLTLSVTIGQPASISCKSNQSLLDSYGKTYLNWLLQRPGQ

SPKRLIYLVSKLDSGVPDRFTGSGSGTDFTLKISRVEAEDLGVYYC

WQGTHFPRTFGGGTKLEIK
(CDRL1-SEQ ID NO: 10-underline; CDRL2-SEQ ID NO:
11-bold; CDRL3-SEQ ID NO: 12-bold/underline)

10C2-Heavy chain
                                        (SEQ ID NO: 13)
QVQLEQSGPVLVKPGASVKMSCKASGYTFTDYYMNWVKQSHGKSLEWIGV

INPYNGGTSYNQKFKGKATLTVDKSSSTACMELNCLTSEDSA

VYYCTLGAYWGQGTSVTVSS
(CDH1-SEQ ID NO: 14-underline; CDH2-SEQ ID NO:
15-bold; CDH3-SEQ ID NO: 16-bold/underline)

12B1-Light chain
                                        (SEQ ID NO: 17)
DIVMTQTTASLSTSVGETVTITCRASGNLHSYLTWYQQKQGKSPQLLVY

NAKTLADGVPSRFSGSGSGTQYSLKIDSLQPEDFGSYYC

QHFWTTPFTFGSGTKLEIK
(CDRL1-SEQ ID NO: 18-underline; CDRL2-SEQ ID
NO: 19-bold; CDRL3-SEQ ID NO: 20-bold/underline)

12B-1 Heavy chain
                                        (SEQ ID NO: 21)
EVKLEESGTELVKPGASVKLSCKASGYTFTSYWMHWVKQRPGQGLEWI

GNINPTNGGTNYNEKFKFSKATLTVDKSSRTAYMQLSSLTSGD

SAVYYCARRDFITTSGFAYWGQGTLVTVSA
(CDH1-SEQ ID NO: 22-underline; CDH2-SEQ ID NO:
23-bold; CDH3-SEQ ID NO: 24-bold/underline)

13H1 Light chain
                                        (SEQ ID NO: 25)
DIVMTQTPKSMSMSVGERVTLSCKASENVGTYVSWYQQKPEQSPK

VLIYGASNRFTGVPDRFTGSGSATDFTLTISSVQTEDLADYHC

GQSYSYPLTFGAGTKLELK
(CDRL1-SEQ ID NO: 26-underline; CDRL2-SEQ ID
NO: 27-bold; CDRL3-SEQ ID NO: 28-bold/underline)

13H1-Heavy chain
                                        (SEQ ID NO: 29)
QVQLQQSGTELVKPGASVKLSCKASGHTFTSYWMHWVKQRPGQGLE

WIGNINPSNGGTNYNEKFKSKATLTVDKSSSTAYMQLSSLTSEDSA

VYYCARRGYYGSSSYWSFDVWGTGTTVTVSS
(CDH1-SEQ ID NO: 30-underline; CDH2-SEQ ID
NO: 31-bold; CDH3-SEQ ID NO: 32-bold/underline)

15B8 Light chain
                                        (SEQ ID NO: 33)
DIVMTQTPASLSASVGETVTITCRASGNIHNYLAWYQQKQGKSPQLLV

YNAKTLADGVPSRF SGSGSGTQYSLKINSLQPEDFGSYYC

QHFWSTPFTFGSGTKLEIK
(CDRL1-SEQ ID NO: 34-underline; CDRL2-SEQ ID
NO: 35-bold; CDRL3-SEQ ID NO: 36-bold/underline)

15B8-Heavy chain
                                        (SEQ ID NO: 37)
QVQLEQSGTELVKPGASVKLSCKASGYTFTSYWMHWVKQRPGQGLEWIG

NINPSNGGTNYNEKFKSKATLTVDKSSSTAYMQLSSLTSED

SAIYYCARRNNYYASSPFAYWGQGTLVSVSA
(CDH1-SEQ ID NO: 38-underline; CDH2-SEQ ID
NO: 39-bold; CDH3-SEQ ID NO: 40-bold/underline)
```

The invention claimed is:

1. An isolated antibody or antigen binding fragment thereof capable of binding human CD30 comprising:
(a) a light chain variable domain comprising a CDRL1 region of SEQ ID NO: 2 or a sequence with at least 85% similarity to SEQ ID NO: 2, a CDRL2 region of SEQ ID NO: 3 or a sequence with at least 85% similarity to SEQ ID NO: 3, and a CDRL3 region of SEQ ID NO: 4 or a sequence with at least 85% similarity to SEQ ID NO: 4, and a heavy chain variable domain comprising a CDRH1 region of SEQ ID NO: 6 or a sequence with at least 85% similarity to SEQ ID NO: 6, a CDRH2 region of SEQ ID NO:7 or a sequence with at least 85% similarity to SEQ ID NO: 7, and a CDRH3 region of SEQ ID NO: 8 or a sequence with at least 85% similarity to SEQ ID NO: 8;
(b) a light chain variable domain comprising a CDRL1 region of SEQ ID NO: 10 or a sequence with at least 85% similarity to SEQ ID NO: 10, a CDRL2 region of SEQ ID NO: 11 or a sequence with at least 85% similarity to SEQ ID NO: 11, and a CDRL3 region of SEQ ID NO: 12 or a sequence with at least 85% similarity to SEQ ID NO: 12, and a heavy chain variable domain comprising a CDRH1 region of SEQ ID NO: 14 or a sequence with at least 85% similarity to SEQ ID NO: 14, a CDRH2 region of SEQ ID NO: 15 or a sequence with at least 85% similarity to SEQ ID NO: 15, and a CDRH3 region of GAY or a sequence with at least 85% similarity to GAY;
(c) a light chain variable domain comprising a CDRL1 region of SEQ ID NO: 18 or a sequence with at least 85% similarity to SEQ ID NO: 18, a CDRL2 region of SEQ ID NO: 19 or a sequence with at least 85% similarity to SEQ ID NO: 19, and a CDRL3 region of SEQ ID NO: 20 or a sequence with at least 85% similarity to SEQ ID NO: 20, and a heavy chain variable domain comprising a CDRH1 region of SEQ ID NO: 22 or a sequence with at least 85% similarity to SEQ ID NO: 22, a CDRH2 region of SEQ ID NO: 23 or a sequence with at least 85% similarity to SEQ ID NO: 23, and a CDRH3 region of SEQ ID NO: 24 or a sequence with at least 85% similarity to SEQ ID NO: 24;
(d) a light chain variable domain comprising a CDRL1 region of SEQ ID NO: 26 or a sequence with at least 85% similarity to SEQ ID NO: 26, a CDRL2 region of SEQ ID NO: 27 or a sequence with at least 85% similarity to SEQ ID NO: 27, and a CDRL3 region of SEQ ID NO: 28 or a sequence with at least 85% similarity to SEQ ID NO: 28, and a heavy chain variable domain comprising a CDRH1 region of SEQ ID NO: 30 or a sequence with at least 85% similarity to SEQ ID NO: 30, a CDRH2 region of SEQ ID NO: 31 or a sequence with at least 85% similarity to SEQ ID NO: 31, and a CDRH3 region of SEQ ID NO: 32 or a sequence with at least 85% similarity to SEQ ID NO: 32; or
(e) a light chain variable domain comprising a CDRL1 region of SEQ ID NO: 34 or a sequence with at least 85% similarity to SEQ ID NO: 34, a CDRL2 region of SEQ ID NO: 35 or a sequence with at least 85% similarity to SEQ ID NO: 35, and a CDRL3 region of SEQ ID NO: 36 or a sequence with at least 85% similarity to SEQ ID NO: 36, and a heavy chain variable domain comprising a CDRH1 region of SEQ ID NO: 38 or a sequence with at least 85% similarity to SEQ ID NO: 38, a CDRH2 region of SEQ ID NO:39 or a sequence with at least 85% similarity to SEQ ID NO: 39, and a CDRH3 region of SEQ ID NO: 40 or a sequence with at least 85% similarity to SEQ ID NO: 40.

2. The isolated antibody or antigen binding fragment thereof of claim 1, wherein the antibody or fragment is a monoclonal antibody, a humanized antibody, a single chain variable fragment (scFv) antibody, a single domain antibody, an or a chimeric antibody.

3. The isolated antibody or antigen binding fragment thereof of claim 1, wherein the antibody or fragment thereof is engrafted within a full IgG scaffold or a scFv scaffold.

4. The isolated antibody or antigen binding fragment thereof of claim 3, wherein the scaffold is human in origin.

5. The isolated antibody or antigen binding fragment thereof of claim 1, wherein the antigen binding fragment thereof is a single chain variable fragment (scFv), and wherein the light chain and heavy chain are linked via a linker amino acid sequence.

6. The isolated antibody or antigen binding fragment of claim 5, wherein the single chain variable fragment comprises an amino acid sequence selected from the group consisting of SEQ ID NO: 42 or a sequence with at least 85% similarity to SEQ ID NO: 42, SEQ ID NO: 44 or a sequence with at least 85% similarity to SEQ ID NO: 44, SEQ ID NO: 46 or a sequence with at least 85% similarity to SEQ ID NO: 46, SEQ ID NO: 48 or a sequence with at least 85% similarity to SEQ ID NO: 48, SEQ ID NO: 50 or a sequence with at least 85% similarity to SEQ ID NO: 50, and SEQ ID NO: 52 or a sequence with at least 85% similarity to SEQ ID NO: 52.

7. A composition comprising the antibody or antigen binding fragment thereof of claim 1 and a pharmaceutically acceptable carrier.

8. The isolated antibody or antigen binding fragment thereof of claim 1, wherein the CD30 antibody or antigen binding fragment thereof comprises:
(a) a light chain variable domain comprising a CDRL1 region of SEQ ID NO: 2 or a sequence with at least 90% similarity to SEQ ID NO: 2, a CDRL2 region of SEQ ID NO: 3 or a sequence with at least 90% similarity to SEQ ID NO: 3, and a CDRL3 region of SEQ ID NO: 4 or a sequence with at least 90% similarity to SEQ ID NO: 4 and a heavy chain variable domain comprising a CDRH1 region of SEQ ID NO: 6 or a sequence with at least 90% similarity to SEQ ID NO: 6, a CDRH2 region of SEQ ID NO: 7 or a sequence with at least 90% similarity to SEQ ID NO: 7, and a CDRH3 region of SEQ ID NO: 8 or a sequence with at least 90% similarity to SEQ ID NO: 8;

(b) a light chain variable domain comprising a CDRL1 region of SEQ ID NO: 10 or a sequence with at least 90% similarity to SEQ ID NO: 10, a CDRL2 region of SEQ ID NO: 11 or a sequence with at least 90% similarity to SEQ ID NO: 11, and a CDRL3 region of SEQ ID NO: 12 or a sequence with at least 90% similarity to SEQ ID NO: 12 and a heavy chain variable domain comprising a CDRH1 region of SEQ ID NO: 14 or a sequence with at least 90% similarity to SEQ ID NO: 14, a CDRH2 region of SEQ ID NO: 15 or a sequence with at least 90% similarity to SEQ ID NO:15, and a CDRH3 region of GAY or a sequence with at least 90% similarity to GAY;

(c) a light chain variable domain comprising a CDRL1 region of SEQ ID NO: 18 or a sequence with at least 90% similarity to SEQ ID NO: 18, a CDRL2 region of SEQ ID NO: 19 or a sequence with at least 90% similarity to SEQ ID NO: 19, and a CDRL3 region of SEQ ID NO: 20 or a sequence with at least 90% similarity to SEQ ID NO: 20 and a heavy chain variable domain comprising a CDRH1 region of SEQ ID NO: 22 or a sequence with at least 90% similarity to SEQ ID NO: 22, a CDRH2 region of SEQ ID NO: 23 or a sequence with at least 90% similarity to SEQ ID NO: 23, and a CDRH3 region of SEQ ID NO: 24 or a sequence with at least 90% similarity to SEQ ID NO: 24;

(d) a light chain variable domain comprising a CDRL1 region of SEQ ID NO: 26 or a sequence with at least 90% similarity to SEQ ID NO: 26, a CDRL2 region of SEQ ID NO: 27 or a sequence with at least 90% similarity to SEQ ID NO: 27, and a CDRL3 region of SEQ ID NO: 28 or a sequence with at least 90% similarity to SEQ ID NO: 28 and a heavy chain variable domain comprising a CDRH1 region of SEQ ID NO: 30 or a sequence with at least 90% similarity to SEQ ID NO: 30, a CDRH2 region of SEQ ID NO: 31 or a sequence with at least 90% similarity to SEQ ID NO: 31, and a CDRH3 region of SEQ ID NO: 32 or a sequence with at least 90% similarity to SEQ ID NO: 32; or (e) a light chain variable domain comprising a CDRL1 region of SEQ ID NO: 34 or a sequence with at least 90% similarity to SEQ ID NO: 34, a CDRL2 region of SEQ ID NO: 35 or a sequence with at least 90% similarity to SEQ ID NO: 35, and a CDRL3 region of SEQ ID NO: 36 or a sequence with at least 90% similarity to SEQ ID NO: 36 and a heavy chain variable domain comprising a CDRH1 region of SEQ ID NO: 38 or a sequence with at least 90% similarity to SEQ ID NO: 38, a CDRH2 region of SEQ ID NO: 39 or a sequence with at least 90% similarity to SEQ ID NO: 39, and a CDRH3 region of SEQ ID NO: 40 or a sequence with at least 90% similarity to SEQ ID NO: 40.

9. The isolated antibody or antigen binding fragment thereof of claim 1, wherein the CD30 antibody or antigen binding fragment thereof comprises:

(a) a light chain variable domain comprising a CDRL1 region of SEQ ID NO: 2 or a sequence with at least 95% similarity to SEQ ID NO: 2, a CDRL2 region of SEQ ID NO: 3 or a sequence with at least 95% similarity to SEQ ID NO: 3, and a CDRL3 region of SEQ ID NO: 4 or a sequence with at least 95% similarity to SEQ ID NO: 4 and a heavy chain variable domain comprising a CDRH1 region of SEQ ID NO: 6 or a sequence with at least 95% similarity to SEQ ID NO: 6, a CDRH2 region of SEQ ID NO: 7 or a sequence with at least 95% similarity to SEQ ID NO: 7, and a CDRH3 region of SEQ ID NO: 8 or a sequence with at least 95% similarity to SEQ ID NO: 8;

(b) a light chain variable domain comprising a CDRL1 region of SEQ ID NO: 10 or a sequence with at least 95% similarity to SEQ ID NO: 10, a CDRL2 region of SEQ ID NO: 11 or a sequence with at least 95% similarity to SEQ ID NO: 11, and a CDRL3 region of SEQ ID NO: 12 or a sequence with at least 95% similarity to SEQ ID NO: 12 and a heavy chain variable domain comprising a CDRH1 region of SEQ ID NO: 14 or a sequence with at least 95% similarity to SEQ ID NO: 14, a CDRH2 region of SEQ ID NO: 15 or a sequence with at least 95% similarity to SEQ ID NO: 15, and a CDRH3 region of GAY or a sequence with at least 95% similarity to GAY;

(c) a light chain variable domain comprising a CDRL1 region of SEQ ID NO: 18 or a sequence with at least 95% similarity to SEQ ID NO: 18, a CDRL2 region of SEQ ID NO: 19 or a sequence with at least 95% similarity to SEQ ID NO: 19, and a CDRL3 region of SEQ ID NO: 20 or a sequence with at least 95% similarity to SEQ ID NO: 20 and a heavy chain variable domain comprising a CDRH1 region of SEQ ID NO: 22 or a sequence with at least 95% similarity to SEQ ID NO: 22, a CDRH2 region of SEQ ID NO: 23 or a sequence with at least 95% similarity to SEQ ID NO: 23, and a CDRH3 region of SEQ ID NO: 24 or a sequence with at least 95% similarity to SEQ ID NO: 24;

(d) a light chain variable domain comprising a CDRL1 region of SEQ ID NO: 26 or a sequence with at least 95% similarity to SEQ ID NO: 26, a CDRL2 region of SEQ ID NO: 27 or a sequence with at least 95% similarity to SEQ ID NO: 27, and a CDRL3 region of SEQ ID NO: 28 or a sequence with at least 95% similarity to SEQ ID NO: 28 and a heavy chain variable domain comprising a CDRH1 region of SEQ ID NO: 30 or a sequence with at least 95% similarity to SEQ ID NO: 30, a CDRH2 region of SEQ ID NO: 31 or a sequence with at least 95% similarity to SEQ ID NO: 31, and a CDRH3 region of SEQ ID NO: 32 or a sequence with at least 95% similarity to SEQ ID NO: 32; or (e) a light chain variable domain comprising a CDRL1 region of SEQ ID NO: 34 or a sequence with at least 95% similarity to SEQ ID NO: 34, a CDRL2 region of SEQ ID NO: 35 or a sequence with at least 95% similarity to SEQ ID NO: 35, and a CDRL3 region of SEQ ID NO: 36 or a sequence with at least 95% similarity to SEQ ID NO: 36 and a heavy chain variable domain comprising a CDRH1 region of SEQ ID NO: 38 or a sequence with at least 95% similarity to SEQ ID NO: 38, a CDRH2 region of SEQ ID NO: 39 or a sequence with at least 95% similarity to SEQ ID NO: 39, and a CDRH3 region of SEQ ID NO: 40 or a sequence with at least 95% similarity to SEQ ID NO: 40.

10. The isolated antibody or antigen binding fragment thereof of claim 1, wherein the CD30 antibody or antigen binding fragment thereof comprises:

(a) a light chain variable domain comprising a CDRL1 region of SEQ ID NO: 2 or a sequence with at least 98% similarity to SEQ ID NO: 2, a CDRL2 region of SEQ ID NO: 3 or a sequence with at least 98% similarity to SEQ ID NO: 3, and a CDRL3 region of SEQ ID NO: 4 or a sequence with at least 98% similarity to SEQ ID NO: 4 and a heavy chain variable domain comprising a CDRH1 region of SEQ ID NO: 6 or a sequence with at least 98% similarity to SEQ ID NO: 6, a CDRH2 region of SEQ ID NO: 7 or a sequence with at least 98% similarity to SEQ ID NO: 7, and a CDRH3 region of SEQ ID NO: 8 or a sequence with at least 98% similarity to SEQ ID NO: 8;

(b) a light chain variable domain comprising a CDRL1 region of SEQ ID NO: 10 or a sequence with at least 98% similarity to SEQ ID NO: 10, a CDRL2 region of SEQ ID NO: 11 or a sequence with at least 98% similarity to SEQ ID NO: 11, and a CDRL3 region of SEQ ID NO: 12 or a sequence with at least 98% similarity to SEQ ID NO: 12 and a heavy chain variable domain comprising a CDRH1 region of SEQ ID NO: 14 or a sequence with at least 98% similarity to SEQ ID NO: 14, a CDRH2 region of SEQ ID NO: 15 or a sequence with at least 98% similarity to SEQ ID NO: 15, and a CDRH3 region of GAY or a sequence with at least 98% similarity to GAY;

(c) a light chain variable domain comprising a CDRL1 region of SEQ ID NO: 18 or a sequence with at least 98% similarity to SEQ ID NO: 18, a CDRL2 region of SEQ ID NO: 19 or a sequence with at least 98% similarity to SEQ ID NO: 19, and a CDRL3 region of SEQ ID NO: 20 or a sequence with at least 98% similarity to SEQ ID NO: 20 and a heavy chain variable domain comprising a CDRH1 region of SEQ ID NO: 22 or a sequence with at least 98% similarity to SEQ ID NO: 22, a CDRH2 region of SEQ ID NO: 23 or a sequence with at least 98% similarity to SEQ ID NO: 23, and a CDRH3 region of SEQ ID NO: 24 or a sequence with at least 98% similarity to SEQ ID NO: 24;

(d) a light chain variable domain comprising a CDRL1 region of SEQ ID NO: 26 or a sequence with at least 98% similarity to SEQ ID NO: 26, a CDRL2 region of SEQ ID NO: 27 or a sequence with at least 98% similarity to SEQ ID NO: 27, and a CDRL3 region of SEQ ID NO: 28 or a sequence with at least 98% similarity to SEQ ID NO: 28 and a heavy chain variable domain comprising a CDRH1 region of SEQ ID NO: 30 or a sequence with at least 98% similarity to SEQ ID NO: 30, a CDRH2 region of SEQ ID NO: 31 or a sequence with at least 98% similarity to SEQ ID NO: 31, and a CDRH3 region of SEQ ID NO: 32 or a sequence with at least 98% similarity to SEQ ID NO: 32; or (e) a light chain variable domain comprising a CDRL1 region of SEQ ID NO: 34 or a sequence with at least 98% similarity to SEQ ID NO: 34, a CDRL2 region of SEQ ID NO: 35 or a sequence with at least 98% similarity to SEQ ID NO: 35, and a CDRL3 region of SEQ ID NO: 36 or a sequence with at least 98% similarity to SEQ ID NO: 36 and a heavy chain variable domain comprising a CDRH1 region of SEQ ID NO: 38 or a sequence with at least 98% similarity to SEQ ID NO: 38, a CDRH2 region of SEQ ID NO: 39 or a sequence with at least 98% similarity to SEQ ID NO: 39, and a CDRH3 region of SEQ ID NO: 40 or a sequence with at least 98% similarity to SEQ ID NO: 40.

11. The isolated antibody or antigen binding fragment thereof of claim 1, wherein the anti-CD30 antibody or antigen binding fragment thereof comprises a light chain and a heavy chain comprising:

(a) a light chain comprising SEQ ID NO: 1 or a sequence with at least 90% similarity to SEQ ID NO: 1, and a heavy chain comprising SEQ ID NO: 5 or a sequence with at least 90% similarity to SEQ ID NO: 5;

(b) a light chain comprising SEQ ID NO: 9 or a sequence with at least 90% similarity to SEQ ID NO: 9, and a heavy chain comprising SEQ ID NO: 13 or a sequence with at least 90% similarity to SEQ ID NO: 13;

(c) a light chain comprising SEQ ID NO: 17 or a sequence with at least 90% similarity to SEQ ID NO: 17, and a heavy chain comprising SEQ ID NO: 21 or a sequence with at least 90% similarity to SEQ ID NO: 21;

(d) a light chain comprising SEQ ID NO: 25 or a sequence with at least 90% similarity to SEQ ID NO: 25, and a heavy chain comprising SEQ ID NO: 29 or a sequence with at least 90% similarity to SEQ ID NO: 29; or (e) a light chain comprising SEQ ID NO: 33 or a sequence with at least 90% similarity to SEQ ID NO: 33, and a heavy chain comprising SEQ ID NO: 37 or a sequence with at least 90% similarity to SEQ ID NO: 37.

12. The isolated antibody or antigen binding fragment thereof of claim 1, wherein the anti-CD30 antibody or antigen binding fragment thereof comprises a light chain and a heavy chain comprising:

(a) a light chain comprising SEQ ID NO: 1 or a sequence with at least 95% similarity to SEQ ID NO: 1, and a heavy chain comprising SEQ ID NO: 5 or a sequence with at least 95% similarity to SEQ ID NO: 5;

(b) a light chain comprising SEQ ID NO: 9 or a sequence with at least 95% similarity to SEQ ID NO: 9, and a heavy chain comprising SEQ ID NO: 13 or a sequence with at least 95% similarity to SEQ ID NO: 13;

(c) a light chain comprising SEQ ID NO: 17 or a sequence with at least 95% similarity to SEQ ID NO: 17, and a heavy chain comprising SEQ ID NO: 21 or a sequence with at least 95% similarity to SEQ ID NO: 21;

(d) a light chain comprising SEQ ID NO:25 or a sequence with at least 95% similarity to SEQ ID NO: 25, and a heavy chain comprising SEQ ID NO: 29 or a sequence with at least 95% similarity to SEQ ID NO: 29; or (e) a light chain comprising SEQ ID NO: 33 or a sequence with at least 95% similarity to SEQ ID NO: 33, and a heavy chain comprising SEQ ID NO: 37 or a sequence with at least 95% similarity to SEQ ID NO: 37.

13. The isolated antibody or antigen binding fragment thereof of claim 1, wherein the anti-CD30 antibody or antigen binding fragment thereof comprises a light chain and a heavy chain comprising:

(a) a light chain comprising SEQ ID NO: 1 or a sequence with at least 98% similarity to SEQ ID NO: 1, and a heavy chain comprising SEQ ID NO: 5 or a sequence with at least 98% similarity to SEQ ID NO: 5;

(b) a light chain comprising SEQ ID NO: 9 or a sequence with at least 98% similarity to SEQ ID NO: 9, and a heavy chain comprising SEQ ID NO: 13 or a sequence with at least 98% similarity to SEQ ID NO: 13;

(c) a light chain comprising SEQ ID NO: 17 or a sequence with at least 98% similarity to SEQ ID NO: 17, and a heavy chain comprising SEQ ID NO: 21 or a sequence with at least 98% similarity to SEQ ID NO: 21;

(d) a light chain comprising SEQ ID NO: 25 or a sequence with at least 98% similarity to SEQ ID NO: 25, and a heavy chain comprising SEQ ID NO: 29 or a sequence with at least 98% similarity to SEQ ID NO: 29; or (e) a light chain comprising SEQ ID NO: 33 or a sequence with at least 98% similarity to SEQ ID NO: 33, and a heavy chain comprising SEQ ID NO: 37 or a sequence with at least 98% similarity to SEQ ID NO: 37.

14. The isolated antibody or antigen binding fragment thereof of claim 1, wherein the anti-CD30 antibody or antigen binding portion thereof comprises a light chain and a heavy chain comprising:
    (a) a light chain comprising SEQ ID NO: 1 and a heavy chain comprising SEQ ID NO: 5;
    (b) a light chain comprising SEQ ID NO: 9 and a heavy chain comprising SEQ ID NO: 13;
    (c) a light chain comprising SEQ ID NO: 17 and a heavy chain comprising SEQ ID NO: 21;
    (d) a light chain comprising SEQ ID NO: 25 and a heavy chain comprising SEQ ID NO: 29; or
    (e) a light chain comprising SEQ ID NO: 33 and a heavy chain comprising SEQ ID NO: 37.

15. The isolated antibody or antigen binding fragment of claim 1, wherein the anti-CD30 antibody or antigen binding fragment thereof comprises a single chain variable fragment comprising:
    SEQ ID NO: 42 or a sequence with at least 90% similarity to SEQ ID NO: 42;
    SEQ ID NO: 44 or a sequence with at least 90% similarity to SEQ ID NO: 44;
    SEQ ID NO: 46 or a sequence with at least 90% similarity to SEQ ID NO: 46;
    SEQ ID NO: 48 or a sequence with at least 90% similarity to SEQ ID NO: 48;
    SEQ ID NO: 50 or a sequence with at least 90% similarity to SEQ ID NO: 50; or
    SEQ ID NO: 52 or a sequence with at least 90% similarity to SEQ ID NO: 52.

16. The isolated antibody or antigen binding fragment of claim 1, wherein the anti-CD30 antibody or antigen binding fragment thereof comprises a single chain variable fragment comprising:
    SEQ ID NO: 42 or a sequence with at least 95% similarity to SEQ ID NO: 42;
    SEQ ID NO: 44 or a sequence with at least 95% similarity to SEQ ID NO: 44;
    SEQ ID NO: 46 or a sequence with at least 95% similarity to SEQ ID NO: 46;
    SEQ ID NO: 48 or a sequence with at least 95% similarity to SEQ ID NO: 48;
    SEQ ID NO: 50 or a sequence with at least 95% similarity to SEQ ID NO: 50; or
    SEQ ID NO: 52 or a sequence with at least 95% similarity to SEQ ID NO: 52.

17. The isolated antibody or antigen binding fragment of claim 1, wherein the anti-CD30 antibody or antigen binding fragment thereof comprises a single chain variable fragment comprising:
    SEQ ID NO: 42 or a sequence with at least 98% similarity to SEQ ID NO: 42;
    SEQ ID NO: 44 or a sequence with at least 98% similarity to SEQ ID NO: 44;
    SEQ ID NO: 46 or a sequence with at least 98% similarity to SEQ ID NO: 46;
    SEQ ID NO: 48 or a sequence with at least 98% similarity to SEQ ID NO: 48;
    SEQ ID NO: 50 or a sequence with at least 98% similarity to SEQ ID NO: 50; or
    SEQ ID NO: 52 or a sequence with at least 98% similarity to SEQ ID NO: 52.

18. A chimeric antigen receptor (CAR) comprising a CD30 binding domain, a hinge region, a transmembrane domain, a costimulatory domain, and an intracellular signaling domain,
    wherein the intracellular domain comprises a CD3 zeta chain, and
    wherein the CD30 binding domain comprises:
    (a) a light chain variable domain comprising a CDRL1 region of SEQ ID NO: 2 or a sequence with at least 85% similarity to SEQ ID NO: 2, a CDRL2 region of SEQ ID NO: 3 or a sequence with at least 85% similarity to SEQ ID NO: 3, and a CDRL3 region of SEQ ID NO: 4 or a sequence with at least 85% similarity to SEQ ID NO: 4, and a heavy chain variable domain comprising a CDRH1 region of SEQ ID NO: 6 or a sequence with at least 85% similarity to SEQ ID NO: 6, a CDRH2 region of SEQ ID NO: 7 or a sequence with at least 85% similarity to SEQ ID NO: 7, and a CDRH3 region of SEQ ID NO:8 or a sequence with at least 85% similarity to SEQ ID NO: 8;
    (b) a light chain variable domain comprising a CDRL1 region of SEQ ID NO: 10 or a sequence with at least 85% similarity to SEQ ID NO: 10, a CDRL2 region of SEQ ID NO: 11 or a sequence with at least 85% similarity to SEQ ID NO: 11, and a CDRL3 region of SEQ ID NO: 12 or a sequence with at least 85% similarity to SEQ ID NO: 12, and a heavy chain variable domain comprising a CDRH1 region of SEQ ID NO: 14 or a sequence with at least 85% similarity to SEQ ID NO: 14, a CDRH2 region of SEQ ID NO: 15 or a sequence with at least 85% similarity to SEQ ID NO: 15, and a CDRH3 region of GAY or a sequence with at least 85% similarity to GAY;
    (c) a light chain variable domain comprising a CDRL1 region of SEQ ID NO: 18 or a sequence with at least 85% similarity to SEQ ID NO: 18, a CDRL2 region of SEQ ID NO: 19 or a sequence with at least 85% similarity to SEQ ID NO: 19, and a CDRL3 region of SEQ ID NO: 20 or a sequence with at least 85% similarity to SEQ ID NO: 20, and a heavy chain variable domain comprising a CDRH1 region of SEQ ID NO: 22 or a sequence with at least 85% similarity to SEQ ID NO: 22, a CDRH2 region of SEQ ID NO: 23 or a sequence with at least 85% similarity to SEQ ID NO: 23, and a CDRH3 region of SEQ ID NO: 24 or a sequence with at least 85% similarity to SEQ ID NO: 24;
    (d) a light chain variable domain comprising a CDRL1 region of SEQ ID NO: 26 or a sequence with at least 85% similarity to SEQ ID NO: 26, a CDRL2 region of SEQ ID NO: 27 or a sequence with at least 85% similarity to SEQ ID NO: 27, and a CDRL3 region of SEQ ID NO: 28 or a sequence with at least 85% similarity to SEQ ID NO: 28, and a heavy chain variable domain comprising a CDRH1 region of SEQ ID NO: 30 or a sequence with at least 85% similarity to SEQ ID NO: 30, a CDRH2 region of SEQ ID NO: 31 or a sequence with at least 85% similarity to SEQ ID NO: 31, and a CDRH3 region of SEQ ID NO: 32 or a sequence with at least 85% similarity to SEQ ID NO: 32; or
    (e) a light chain variable domain comprising a CDRL1 region of SEQ ID NO: 34 or a sequence with at least 85% similarity to SEQ ID NO: 34, a CDRL2 region of SEQ ID NO: 35 or a sequence with at least 85% similarity to SEQ ID NO: 35, and a CDRL3 region of SEQ ID NO: 36 or a sequence with at least 85% similarity to SEQ ID NO: 36, and a heavy chain variable domain comprising a CDRH1 region of SEQ ID NO: 38 or a sequence with at least 85% similarity to SEQ ID NO: 38, a CDRH2 region of SEQ ID NO: 39 or a sequence with at least 85% similarity to SEQ ID NO: 39, and a CDRH3 region of SEQ ID NO: 40 or a sequence with at least 85% similarity to SEQ ID NO: 40.

19. The CAR of claim 18, wherein the CAR comprises a single chain variable fragment comprising an amino acid sequence of SEQ ID NO: 42 or a sequence with at least 85% similarity to SEQ ID NO: 42, SEQ ID NO: 44 or a sequence with at least 85% similarity to SEQ ID NO: 44, SEQ ID NO: 46 or a sequence with at least 85% similarity to SEQ ID NO: 46, SEQ ID NO: 48 or a sequence with at least 85% similarity to SEQ ID NO: 48, SEQ ID NO: 50 or a sequence with at least 85% similarity to SEQ ID NO: 50, or SEQ ID NO: 52 or a sequence with at least 85% similarity to SEQ ID NO: 52.

20. An isolated antibody or antigen binding fragment thereof which binds human CD30 comprising a light chain variable domain comprising a CDRL1 region of SEQ ID NO: 2, a CDRL2 region of SEQ ID NO: 3, a CDRL3 region of SEQ ID NO: 4, and a heavy chain variable domain comprising a CDRH1 region of SEQ ID NO: 6, a CDRH2 region of SEQ ID NO: 7, and a CDRH3 region of SEQ ID NO: 8.

21. The antibody or antigen binding fragment thereof of claim 20 comprising a light chain comprising SEQ ID NO: 1 or a sequence with at least 95% similarity to SEQ ID NO: 1, and a heavy chain comprising SEQ ID NO: 5 or a sequence with at least 95% similarity to SEQ ID NO: 5.

22. The antibody or antigen binding fragment thereof of claim 20 comprising a light chain comprising SEQ ID NO: 1 or a sequence with at least 98% similarity to SEQ ID NO: 1, and a heavy chain comprising SEQ ID NO: 5 or a sequence with at least 98% similarity to SEQ ID NO: 5.

23. The antibody or antigen binding fragment thereof of claim 20 comprising a light chain comprising the amino acid sequence of SEQ ID NO: 1 and a heavy chain comprising the amino acid sequence of SEQ ID NO: 5.

24. The antibody or antigen binding fragment thereof of claim 20 comprising a single chain variable fragment comprising the amino acid sequence of SEQ ID NO: 42 or a sequence with at least 85% similarity to SEQ ID NO: 42 or 44.

25. The antibody or antigen binding fragment thereof of claim 20 comprising a single chain variable fragment comprising the amino acid sequence of SEQ ID NO: 42 or a sequence with at least 90% similarity to SEQ ID NO: 42 or 44.

26. The antibody or antigen binding fragment thereof of claim 20 comprising a single chain variable fragment comprising the amino acid sequence of SEQ ID NO: 42 or a sequence with at least 95% similarity to SEQ ID NO: 42 or 44.

27. The antibody or antigen binding fragment thereof of claim 20 comprising a single chain variable fragment comprising the amino acid sequence of SEQ ID NO: 42 or a sequence with at least 98% similarity to SEQ ID NO: 42 or 44.

28. The antibody or antigen binding fragment thereof of claim 20 comprising a single chain variable fragment comprising the amino acid sequence of SEQ ID NO: 42 or 44.

29. The antibody or antigen binding fragment thereof of claim 20, wherein the antibody is a monoclonal antibody, a humanized antibody, a single chain variable fragment (scFv), a single domain antibody, or a chimeric antibody.

30. The antibody or antigen binding fragment thereof of claim 20, wherein the antibody or antigen-binding fragment thereof is engrafted within a full IgG scaffold or a scFv scaffold.

31. The antibody or antigen binding fragment thereof of claim 20, wherein the scaffold is human in origin.

32. The antibody or antigen binding fragment thereof of claim 20, wherein the antigen binding fragment thereof is a single chain variable fragment (scFv) wherein the light chain and heavy chain are linked via a linker amino acid sequence.

33. A composition comprising the antibody or antigen binding fragment thereof of claim 20 and a pharmaceutically acceptable carrier.

34. An isolated antibody or antigen binding fragment thereof which binds human CD30 comprising a light chain variable domain comprising a CDRL1 region comprising the sequence of SEQ ID NO: 10, a CDRL2 region comprising the sequence of SEQ ID NO: 11, and a CDRL3 region comprising the sequence of SEQ ID NO: 12, and a heavy chain variable domain comprising the sequence of SEQ ID NO: 14, a CDRH2 region comprising the sequence of SEQ ID NO: 15, and a CDRH3 region comprising the sequence of GAY.

35. The antibody or antigen binding fragment thereof of claim 34 comprising a light chain comprising SEQ ID NO: 9 or a sequence with at least 95% similarity to SEQ ID NO: 9, and a heavy chain comprising SEQ ID NO: 13 or a sequence with at least 95% similarity to SEQ ID NO: 13.

36. The antibody or antigen binding fragment thereof of claim 34 comprising a light chain comprising SEQ ID NO: 9 or a sequence with at least 98% similarity to SEQ ID NO: 9, and a heavy chain comprising SEQ ID NO: 13 or a sequence with at least 98% similarity to SEQ ID NO: 13.

37. The antibody or antigen binding fragment thereof of claim 34 comprising a light chain comprising the amino acid sequence of SEQ ID NO: 9 and a heavy chain comprising the amino acid sequence of SEQ ID NO: 13.

38. The antibody or antigen binding fragment thereof of claim 34 comprising a single chain variable fragment comprising the amino acid sequence of SEQ ID NO: 46.

39. The antibody or antigen binding fragment thereof of claim 34, wherein the antibody is a monoclonal antibody, a humanized antibody, a single chain variable fragment (scFv), a single domain antibody, or a chimeric antibody.

40. The antibody or antigen binding fragment thereof of claim 34, wherein the antibody or antigen-binding fragment thereof is engrafted within a full IgG scaffold or a scFv scaffold.

41. The antibody or antigen binding fragment thereof of claim 34, wherein the scaffold is human in origin.

42. The antibody or antigen binding fragment thereof of claim 34, wherein the antigen binding fragment thereof is a single chain variable fragment (scFv) wherein the light chain and heavy chain are linked via a linker amino acid sequence.

43. A composition comprising the antibody or antigen binding fragment thereof of claim 34 and a pharmaceutically acceptable carrier.

* * * * *